US008173786B2

(12) United States Patent
Weiner et al.

(10) Patent No.: US 8,173,786 B2
(45) Date of Patent: May 8, 2012

(54) NUCLEIC ACID SEQUENCES ENCODING AND COMPOSITIONS COMPRISING IGE SIGNAL PEPTIDE AND/OR IL-15 AND METHODS FOR USING THE SAME

(75) Inventors: David B. Weiner, Merion, PA (US); Michele Kutzler, Souderton, PA (US); Andrew Y. Choo, Boston, MA (US); Joo-Sung Yang, Suwon (KR); Jean D. Boyer, Haddonfield, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 962 days.

(21) Appl. No.: 10/560,650

(22) PCT Filed: Jun. 14, 2004

(86) PCT No.: PCT/US2004/018962
§ 371 (c)(1), (2), (4) Date: May 9, 2006

(87) PCT Pub. No.: WO2005/000235
PCT Pub. Date: Jan. 6, 2005

(65) Prior Publication Data
US 2007/0041941 A1 Feb. 22, 2007

Related U.S. Application Data

(60) Provisional application No. 60/478,205, filed on Jun. 13, 2003, provisional application No. 60/478,210, filed on Jun. 13, 2003.

(51) Int. Cl.
*C07H 21/02* (2006.01)
*C07H 21/04* (2006.01)
*C12N 15/00* (2006.01)

(52) U.S. Cl. .................................... 536/23.1; 435/320.1
(58) Field of Classification Search ................. 536/23.1; 435/320.1
See application file for complete search history.

(56) References Cited

U.S. PATENT DOCUMENTS

| | | | |
|---|---|---|---|
| 4,722,848 A | 2/1988 | Paoletti et al. | |
| 4,945,050 A | 7/1990 | Sanford et al. | |
| 5,017,487 A | 5/1991 | Stunnenberg et al. | |
| 5,036,006 A | 7/1991 | Sanford et al. | |
| 5,077,044 A | 12/1991 | Stocker et al. | |
| 5,110,587 A | 5/1992 | Paoletti et al. | |
| 5,112,749 A | 5/1992 | Brey et al. | |
| 5,174,993 A | 12/1992 | Paoletti et al. | |
| 5,223,424 A | 6/1993 | Cochran et al. | |
| 5,225,336 A | 7/1993 | Paoletti et al. | |
| 5,240,703 A | 8/1993 | Cochran et al. | |
| 5,242,829 A | 9/1993 | Panicali et al. | |
| 5,294,441 A | 3/1994 | Curtiss et al. | |
| 5,294,548 A | 3/1994 | McLinden et al. | |
| 5,310,668 A | 5/1994 | Ellis et al. | |
| 5,387,744 A | 2/1995 | Curtiss et al. | |
| 5,389,368 A | 2/1995 | Curtiss et al. | |
| 5,424,065 A | 6/1995 | Curtiss et al. | |
| 5,451,499 A | 9/1995 | Cochran et al. | |
| 5,453,364 A | 9/1995 | Paoletti et al. | |
| 5,462,734 A | 10/1995 | Letchworth et al. | |
| 5,470,734 A | 11/1995 | Sondermeijer et al. | |
| 5,482,713 A | 1/1996 | Paoletti et al. | |
| 5,580,859 A | 12/1996 | Felgner et al. | |
| 5,593,972 A | 1/1997 | Weiner et al. | |
| 5,676,594 A | 10/1997 | Joosten et al. | |
| 5,703,055 A | 12/1997 | Felgner et al. | |
| 5,739,118 A | 4/1998 | Carrano et al. | |
| 5,817,637 A | 10/1998 | Weiner et al. | |
| 5,830,876 A | 11/1998 | Weiner et al. | |
| 5,840,530 A | 11/1998 | Gubler et al. | |
| 5,962,428 A | 10/1999 | Carrano et al. | |
| 5,981,505 A | 11/1999 | Weiner et al. | |
| 2002/0123099 A1* | 9/2002 | Weiner et al. ................. | 435/69.1 |
| 2006/0052592 A1* | 3/2006 | Levinson et al. ............. | 536/23.1 |

FOREIGN PATENT DOCUMENTS

| | | | |
|---|---|---|---|
| WO | PCT/US94/00899 | | 8/1994 |
| WO | PCT/US98/20321 | * | 9/1998 |
| WO | WO 01/24818 A | | 4/2001 |
| WO | WO 01/85920 A | | 11/2001 |
| WO | WO 02/29088 A2 | | 4/2002 |
| WO | 03017935 | | 3/2003 |

OTHER PUBLICATIONS

Armitage et al., IL-15 has stimulatory activity for the induction of B cell proliferation and differentiation. J Immunol. 154(2):483-90, 1995.*
Yang et sl.,Induction of potent Th1-type immune responses from a novel DNA vaccine for West Nile virus New York isolate (WNV-NY1999). J Infect Dis. 184(7):809-16, 2001.*
Hu, Non-human primate models for AIDS vaccine research. Curr Drug Targets Infect Disord. 5(2):193-201, 2005.*
Belakova et al., DNA vaccines: are they still just a powerful tool for the future? Arch Immunol Ther Exp (Warsz). 55(6):387-98, 2007.*
Yang et al., Induction of inflammation by West Nile virus capsid through the caspase-9 apoptotic pathway. Emerg Infect Dis. 8(12):1379-84, 2002.*
Mittendorf et al.,Breast cancer vaccines: promise for the future or pipe dream? Cancer. 110(8):1677-86, 2007.*
Yang et al., Induction of inflammation by West Nile virus capsid through the caspase-9 apoptotic pathway. Emerg Infect Dis. 8(12):1379-84, 2002.*
Ulmer et al., Gene-based vaccines: recent technical and clinical advances. Trends Mol Med. 12(5):216-22, 2006.*

(Continued)

*Primary Examiner* — Wu-Cheng Winston Shen
(74) *Attorney, Agent, or Firm* — Pepper Hamilton, LLP

(57) ABSTRACT

Fusion proteins and nucleic acid molecules encoding fusion proteins are disclosed. Fusion proteins comprising non-IL-15 signal peptide linked to IL-15 protein sequences and fusion proteins comprising an IgE signal peptide linked to non-IgE protein sequences are disclosed. Vectors comprising such nucleic acid molecules; and to host cells comprising such vectors are disclosed as well as recombinant vaccines and live attenuated pathogens encoding fusion proteins, and methods of using the same, are disclosed. The immunomodulatory effect following delivery of IL-15 and CD40L, with or without immunogens, is disclosed as are various nucleic acid molecules and compositions thereof used for delivering such proteins and methods of using such compositions.

19 Claims, 18 Drawing Sheets

OTHER PUBLICATIONS

Meazza et al., Expression of two interleukin-15 mRNA isoforms in human tumors does not correlate with secretion: role of different signal peptides, Eur J Immunol. 27(5):1049-54, 1997.*

Aarts et al., Vector-based vaccine/cytokine combination therapy to enhance induction of immune responses to a self-antigen and anti-tumor activity, Cancer Res. 62(20):5770-7, 2002.*

Cines et a., In vitro binding of an IgE protein to human platelets, J. Immunol. 136(9):3433-40, 1986.*

Agostini, C., et al. "CD8 T-Cell Infiltration in Extravascular Tissues of Patients with Human Imunodeficiency Virus Infection. Interleukin 15 Upmodulates Co-Stimulatory Pathways Involved in the Antigen Presenting Cells of T-cell Interaction." *Blood*, (1999) 93: 1277-1286.

Anderson, S., et al. "Nef from primary isolates of human immunodeficiency virus type I suppressed surface CD4 expression in human and mouse T cells" *J Virol* (1993) 67 : 4923-493 1.

Anderson D.M. et al., "Chromosomal assignment and genomic structure of I115," *Genomics* (1995), 25(3):701-6.

Anether et al., "Interleukin-15 as a potential costimulatary cytokine in CD154 gene therapy of chronic lymphocytic leukemia," *Blood* (2002) p. 722-723.

Arai, et al., "Complete nucleotide sequence of the chromosomal gene for human IL-4 and its expression," *J. Immunol.* (1989), 142:274-282.

Armitage R.J. et al., "IL-15 has stimulatory activity for the induction of B cell proliferation and differentiation," *J. Immunol* Jan. 15, 1995;154(2):483-90.

Ayyavoo, V., et al., "HIV-1 vpr suppresses immune activation and apoptosis through regulation of nuclear factor KB," *Nature Medicine*, (1997) 3: 1117-1122.

Azuma, et al., "Cloning of cDNA for human T-cell replacing factor (interleukin-5) and comparison with the murine homologue," *Nucl. Acids Res.* (1986), 14:9149-9158.

Bamford R.N. et al., "The neuromuscular blocking activity of some monoquatemary androstane derivatives," *J Pharm Pharmacol* (1971), 23(8):595-9.

Borrow, R., et al 1998, "Cytotoxic lymphocyte escape viral variant how important are they in viral evasions of immune clearance in vivo," *Immunology Rev*, (1998) 164: 37-51.

Bourgeois, C., et al. "A Role for CD40 Expression on CD8+ T Cells in the Generation of CD8+ T Cell Memory," 2002, *Science* 297: 2060-2063.

Campbell, et al., "Molecular cloning, nucleotide sequence, and expression of the gene encoding human eosinophil differentiation factor (interleukin 5)," *Proc. Natl. Acad. Sci. USA* (1987), 84:6629-6633.

Campbell, et al., "Isolation, structure and expression of cDNA and genomic clones for murine eosinophil differentiation factor. Comparison with other eosinophilopoietic lymphokines and identity with interleukin-5," *Eur. J. Biochem.* (1988), 174:345-352.

Cao, H., et al. "Cytotoxic T Lymphocyte Cross-Reactivity among Different HIV-1 Type 1 Clades: Implication for Vaccine Development," *J Virol* ; (1997) 71: 86158623.

Chang, KH, et al. "Spontaneous Programmed Cell Death of Peripheral Blood Mononuclear Cells from HIV-Infected Persons is Decreased with IL-15." *Yonsei Medical Journal*, (2000) 41: 112-118.

Chiu et al., "The c-Fos protein interacts with c-Jun/AP-1 to stimulate transcription of AP-1 responsive genes," *Cell* (1988) 54:541-552.

Chaudhary, V.K. et al., "A rapid method of cloning functional variable-region antibody genes in *Escherichia coli* as single-chain immunotoxins," *Proc. Nat. Acad. Sci. USA* (1990) 87:1066-1070.

Devos, et al., "Molecular cloning of human interleukin 2 cDNA and its expression in *E. coli,*" *Nucl. Acids Res.* (1983) 11:4307-4323.

Finzi, D., et al "Identification of a Reservoir for HIV-1 Patients on Highly Active Antiviral Therapy," *Science*, (1997) 278: 1295-1300.

Franklin et al. "Constitutively active MAP kinase kinase (MEK1) stimulates SAP kinase and c-Jun transcriptional activity in U937 human leukemic cells," *Oncogene*. Dec. 7, 1995;11(11):2365-74.

Furutani, et al., "Complete nucleotide sequence of the gene for human interleukin 1 alpha," *Nucl. Acids Res.* (1985) 14:3167-3179.

Fuse, et al., Organization and structure of the mouse interleukin-2 gene, *Nucl. Acids Res.* (1984), 12:9323-9331.

Gilmore et al.,1 "The I kappa B proteins: members of a multifunctional family,"*Trends Genet* Dec. 1993;9(12):427-33.

Giri J.G. et al., "Utilization of the beta and gamma chains of the IL-2 receptor by the novel cytokine IL-15," *Embo J* (1994), 13(12):2822-30.

Giri et al., "Identification and cloning of a novel IL-15 binding protein that is structurally related to the alpha chain of the IL-2 receptor," *EMBO J.* Aug. 1, 1995;14(15):3654-63.

Goulder PJ, et al "Late escape from an immunodominant cytotoxic T lymphocyte response associated with progression to AIDS," *Nature Medicine*, (1997) 3 ; 212-217.

Goulder PJ, et al "Patterns of immunodominance in HIV-1 specific cytotoxic T lymphocyte response in two human histocompatibility leukocyte antigens HLA identical siblings with HLA A0201 are influence by epitope mutations." *JExp Med*, (1997)185: 1423-1433.

Grabstein K. et al., "Cloning of a T cell growth factor that interacts with the beta chain of the interleukin-2 receptor," *Science* (1994) 264:965.

Gray et al., "Cloning and expression of cDNA for human lymphotoxin, a lymphokine with tumour necrosis activity ," *Nature* (1984), 312:721-724.

Ho, "Therapy of HIV infections: problems and prospects," *Bull. New York Acad. Med.* (1996) 73,37-45.

Holbrook, et al., "T-cell growth factor: complete nucleotide sequence and organization of the gene in normal and malignant cells," *Proc. Natl. Acad. Sci. USA* (1984) 81:1634-1638.

Howell M.D.et al., "Limited T-cell receptor beta-chain heterogeneity among interleukin 2 receptor-positive synovial T cells suggests a role for superantigen in rheumatoid arthritis," *Proc. Nat. Acad. Sci. USA* (1991) 88:10921-10925.

Kacani, L., et al. "Role of IL-15 in HIV-1 Associated Hypergammaglobulinanemia." *Clin Exp Iinm* (1997) 108: 14-18.

Kacani, L., et al. "Interleukin-15 Enhances HIV-1 Driven Polyclonal B-Cell Response in Vitro." *Exp and Clin Immun*, (1999) 16: 167-179.

Kalams, S.A., et al. "The critical need for CD4 help in maintaining effective cytotoxic T Lymphocyte Responses", *J. Exp Med*. (1998) 188(12): 2199-204.

Kerkau, T., et al. "The human immunodeficiency virus type I (HIV-1) vpu protein interferes with an early step in the biosynthesis of major histocompatibility complex (MHC) class I molecules," *J Exp Med.*, (1997) 185: 1295-1305.

Kim, JJ., et al., "Modulation of amplitutude and direction of in vivo immune responses by co-administration of cassettes with DNA immunogens," *Eur. J Immunol.* (1998) 28 : 1089-1103.

Kim JJ., et al. "Intracellular adhesion molecule-1 modulates beta-chemokines and directly costimulates T cells in vivo," *Journal of Clinical Investigation*. (1999) 103: 869-77.

Koup, R., et al "Temporal association of cellular immune responses with the initial control of viremia in primary Human immunodeficiency virus type 1 syndrome" *Jof Virol*, ( 1994) 68: 4650-4655.

Koup, RA, "Virus Escape from CTL recognition," *J Exp Med*, (1994) 180 ; 779-782.

Kozak et al., "An analysis of vertebrate mRNA sequences: intimations of translational control," *J Cell Biol* (1991), 115(4):887-903.

Ku, CC., et al. "Control of Homerostasis of CD8 Memory T Cells by Opposing Cytokines," *Science*, (2000) 288 : 675-678.

Meyer R., et al.,"Cloning of the DNA-binding subunit of human nuclear factor kappa B: the level of its mRNA is strongly regulated by phorbol ester or tumor necrosis factor alpha," *Proc. Natl. Acad. Sci. USA* (1991) 88(3), 966-970.

Moore AC., et al. "Effects of antigen and genetic adjuvants on immune responses to human immunodeficiency virus DNA vaccines in mice." *Journal of Virology*. 76(1) : 243-50, Jan. 2002.

Murali-Krishna, K., et al. "Persistence of Memory CD8 T Cells in MHC Class I-Deficient Mice," *Science*, (1999) 286 : 1377-1383.

Naora H., et al. "Enhanced Survival and Potent Expansion of the Natural Killer Population of HIV Infected Individuals by Exogenous IL-15." *Immunology Letters*, (1999) 68: 359-367.

Noma, et al., "Cloning of cDNA encoding the murine IgG1 induction factor by a novel strategy using SP6 promoter," *Nature* (1986), 319:640-646.

Oksenberg, J.R. et al., "Limited heterogeneity of rearranged T-cell receptor V alpha transcripts in brains of multiple sclerosis patients," *Nature* (1990), 345:344-346.

Otsuka, et al., "Structural analysis of the mouse chromosomal gene encoding interleukin 4 which expresses B cell, T cell and mast cell stimulating activities," *Nucl. Acids Res.* (1987), 15:333-344.

Paliard, X et al., "Evidence for the effects of a superantigen in rheumatoid arthritis," *Science* (1991) 253:325-329.

Patki, AH., et al. "Activation of antigen Inducaed Lymphocute Proliferation by Interleukin-15 Without the Mitogenic Effect og Interleukin-2 That May Induce Human Immunodefeciency Virus-1 Expression." *JCI*, (1996) 98: 616-621.

Pennica et al., "Human tumour necrosis factor: precursor structure, expression and homology to lymphotoxin," *Nature* (1984), 312:724-729.

Phillips RE, et al. "Human immunodeficiency virus genetic variation'that can escape cytotoxic T cell recognition" *Nature*, (1991) 354 ; 453-459.

Rauscher et al.,"Fos-associated protein p39 is the product of the jun proto-oncogene," *Science* 1988 240:1010-1016.

Rinaldo, C. et al "High Levels of Anti-Human Immunodeficiency Virus Type 1 (HIV-1) Memory Cytotoxic T-Lymphocyte Activity and Low Viral Load Are Associated with Lack of Disease in HIV-1 Infected Long-Term Nonprogressors," *J Virol.*, (1995) 69: 5838-5842.

Rosenberg, ES, et al. "Vigorous HIV-1 Specific CD4 T cell Responses Associated with Control of Viremia," *Science*, 278: 1447-1450, (1997).

Rosenberg, ES, et al "Immune control of HIV-1 after early treatment of acute infection," *Nature*, (2000) 407: 523.

Rowland-Jones S., et al "HIV-specific cytotoxic T-cell activity in an HIV-exposed but uninfected infant." *Lancet*, (1993) 341: 860-86.

Rowland-Jones S., et al. "HIV-specific T-cells in HIV-exposed but uninfected Gambian women." *Nature Medicine*, (1995) 1: 59-64 10.

Ruckert et al., "IL-15-IgG2b fusion protein accelerates and enhances a Th2 but not a Th1 immune response in vivo, while IL-2-IgG2b fusion protein inhibits both," *Eur Journal Immunol.* (1998), vol. 28; 3312-3320.

Serbina NV., et al. "CD4 (+) T cells are required for the development of cytotoxic CD8 (+) T cells during Mycobacterium tuberculosis infection." *Journal of Immunology.* (2001) 167: 6991-7000.

Shankar P., et al., "Impaired function of circulating HIV-specific CD8 (+) T cells in chronic human immunodeficiency virus infection." *Blood.* (2000) 96 (9): 3094-101 22.

Sin JI., et al. "Modulation of cellular responses by plasmid CD40L: CD40L plasmid vectors enhance antigen-specific helper T cell type 1 CD4+ T cell-mediated protective immunity against herpes simplex virus type 2 in vivo." *Human Gene Therapy.* 12: 1091-102, 2001.

Tagaya, Y., "A Plenotropic Cytokine with Diverse Receptor/Signaling Pathways Whose Expression is Controlled at Multiple Pathways." *Immunity* (1996) 4: 329-336.

Taniguchi, et al., "Structure and expression of a cloned cDNA for human interleukin-2," *Nature* (1983), 302:305-310.

Tanabe, et al., "Molecular cloning and structure of the human interleukin-5 gene," *J.Biol. Chem.* (1987), 262:16580-16584.

Telford, et al., "The murine interleukin 1 beta gene: structure and evolution," *Nucl. Acids Res.* (1986),1 4:9955-9963.

Ushio, et al., "Cloning of the cDNA for human IFN-gamma-inducing factor, expression in *Escherichia coli*, and studies on the biologic activities of the protein," *J. Immunol.* (1996), 156:4274-4279.

Vieira, et al., "Isolation and expression of human cytokine synthesis inhibitory factor cDNA clones: homology to Epstein-Barr virus open reading frame BCRFI," *Proc. Natl. Acad. Sci. USA* (1991), 88:1172-1176.

Waldmann et al., "The multifaceted regulation of interleukin-15 expression and the role of this cytokine in NK cell differentiation and host response to intracellular pathogens," *Annu Rev Immunol* (1999);17:19-49.

Wierda et al., "CD40-ligand (CD154) gene therapy for chronic lymphocytic leukemia," *Blood* (2000), vol. 96 pp. 2917-2924.

Wilkinson P. and Liew F. "Chemoattraction of human blood T lymphocytes by interleukin-15 ," *J Exp Med* (1995), 181(3):1255-9.

Williams W.V. et al., "Restricted heterogeneity of T cell receptor transcripts in rheumatoid synovium," *J. Clin Invest.*(1992) 90:326-333.

Wong, J., et al "Recovery of Replication-Competent HIV Despite Prolonged Suppression of Plasma Viremia," *Science*, (1997) 278: 1291-1294.

Wucherpfennig, K.W. et al., "Shared human T cell receptor V beta usage to immunodominant regions of myelin basic protein," *Science* (1990) 248:1016-1019.

Yokota, et al., "Isolation and characterization of a human interleukin cDNA clone, homologous to mouse B-cell stimulatory factor 1, that expresses B-cell- and T-cell-stimulating activities," *Proc. Natl. Acad. Sci USA* (1986), 83:5894-5898.

Yokota, et al., "Isolation and characterization of lymphokine cDNA clones encoding mouse and human IgA-enhancing factor and eosinophil colony-stimulating factor activities: relationship to interleukin 5.," *Proc. Natl. Acad. Sci. USA* (1986), 84:7388-7392.

Zhang, X., et al., "Potent and selective stimulation of memory-phenotype CD8+ T cells in vivo by IL-15," *J., Immunity*, (1998) 8: 591-599.

Borrow, P., et al. "Antiviral pressure exerted by HIV-1 specific cytotoxic T lymphocytes during primary infection demonstrated by rapid selection of CTL escape virus" *Nature Medicine*, (1997) 3: 205-211.

Lu et al, "Human immunodeficiency virus type 1 viral protein R localization in infected cells and virions," *J. Virol.* Nov. 1993;67(11):6542-50.

Onu, A.. et al. "Regulation of IL-15 secretion via the leader peptide of two IL-15 isoforms.", *Journal of Immunology*, (1997) 158: 255-262.

Suzuki, K. et al., "NK cell-mediated anti-tumor immune response to human prostate cancer cell, PC-3: imunogene therapy using a highly secretable form of interleukin-15 gene transfer.", *Journal of Leukocyte Biology*, (2001) 69: 531-537.

Yang, J-S et al., "Induction of potent Th1-type immune responses from a novel dna vaccine for west nile virus," *Journal of Infectious Diseases*; (2001) 184:809-816.

Rueckert, R. et al., "IL-15-IgG2b fusion protein accelerates and enhances a Th2 but not a Th1 immune response in vivo, while IL-2-IgG2b fusion protein inhibits both.", *European Journal of Immunology* (1998) 28: 3312-3320.

Lee, et al., "Isolation and characterization of a mouse interleukin cDNA clone that expresses B-cell stimulatory factor 1 activities and T-cell- and mast-cell-stimulating activities," *Proc. Natl. Acad. Sci. USA* (1986) 83:2061-2063.

Lee et al., "Purified transcription factor AP-1 interacts with TPA-inducible enhancer elements," *Cell* (1987) 49:741-752.

Lenburg et al. "VPU induced degradation of CD4: Requirement for specific amino acid residues in the cyotplasmic domain of CD4," *J Virol*, (1993) , 7238-7245.

Lin, SJ, et al. "Human Immunodeficiency Virus (HIV) Type-1 GP120-Specific Cell Mediated Cytotoxicity Interleukin-2 (IL-2), IL-12, and IL-15." *Clin. Imm. Ininipatli*, (1997) 82: 163-173.

Loubeau, M., et al. 1997, "Jo. Enhancement of Natural Killer and Antibody Dependent Cytotoxic Activities of the Peripheral Mononuclear Cells of HIV-Infected Patients by Recombinant IL-15. AIDS" (1997) 16: 137-145.

Lucey DR., et al. "In Vitro Immunologic and Virologic Effects of Interleukin-15 on Peripheral Blood Mononuclear Cells from Normal Donors and Human Immunodeficiency Virus Type-1 Infected Patients." *Clin Diagn Lab Imm*, 4: 43-48, 1997.

Maeda, et al., "Cloning of interleukin 2 mRNAs from human tonsils," *Biochem. Biophys. Res. Comm.* (1983), 115:1040-1047.

Manjunath, N., et al. "Effector differentiation is not prerequisite for generation of memory cytotoxic T lymphocytes, "*Journal of Clinical Investigation*, (2001) 108: 871-878.

March, et al.,"Cloning, sequence and expression of two distinct human interleukin-1 complementary DNAs," *Nature* (1985) 315:641-647.

Mata, M., et al. "The MHC Class I Restricted Immune Response to HIV-1 gag in Balb/c Mice Selects a Single Epitope That Does not Have a Predictable MHC Binding-Motif and Binds to Kd Through Interactions Between a Glutamine at PS and Pocket D," *Jo of Immun.*, (1998) 161: 2985-2993.

McCarrick III JW, et al. "Positive-negative selection gene targeting with the diphtheria toxin A-chain gene in mouse embryonic stem cells." *Transgenic Res* (1993) 2: 183-190.

Meazza, R. et al., "Expression of two interleukin-15 mRNA isoforms in human tumors does not correlate with secretion: role of different signal peptides", Eur. J. Immunol. (1997) 27 (5):1049-1054.

Oh, S. et al., "Coadministration of HIV vaccine vectors with vaccinia viruses expressing IL-15 but not IL-2 induces long-lasting cellular immunity", Proc. Natl. Acad. Sci. USA (2003), 100 (6):3392-3397.

Ostrowski, Mario A. et al., "The Role of CD4+ T Cell Help and CD40 Ligand in the In Vitro Expansion of HIV-1-Specific Memory Cytotoxic CD8+ T Cell Responses", J. Immunol. (2000) 165(11)6133-6141.

PCT Domestic Announement No. 2001-526241, Thomas, WO 99/32138, Jul. 1, 1999.

* cited by examiner

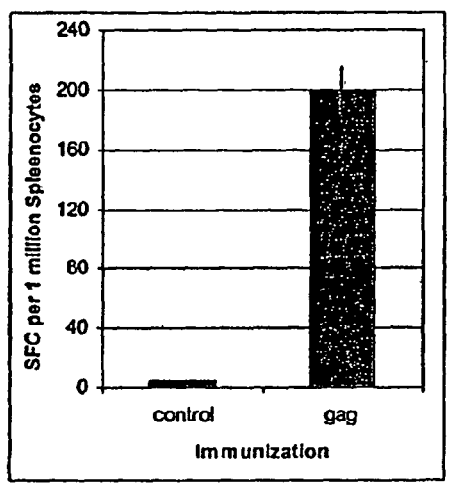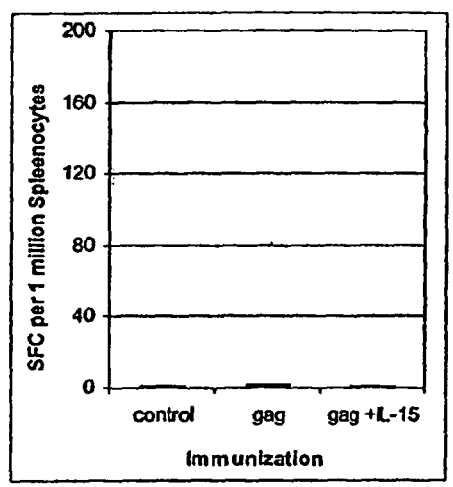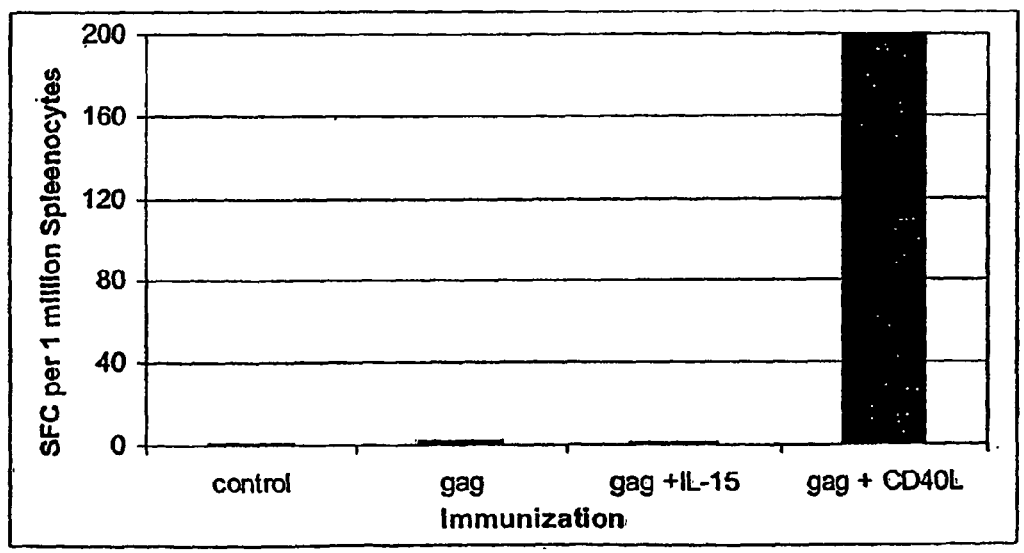
Figure 8

Strategy for Increasing Expression of IL-15 through Optimization of IL-15 DNA Constructs for Immunization

- Primers are designed to amplify IL-15 from start of signal peptide, thus upstream inhibitory AUGs are not present in the final IL-15 message.

- Primers are designed to include a strong KOZAK context (GCCGCCACC)

- Removal of the C-terminus negative regulatory element using PCR antisense primer design

| *Primer Name* | *Sense/Antisense* | *Sequence 5' to 3'* |
|---|---|---|
| Human IL-15 (LSP) | sense (SEQ ID NO:4) | GCCCCC*GTCGAC* GCCGCCACCATGAGAATTTCGAAACCACATTTGAG |
| | antisense (SEQ ID NO:5) | ATCGGG*CTCGAG* TCAAGAAGTGTTGATGAACATTTGG |
| Macaque IL-15 (LSP) | sense (SEQ ID NO:4) | GCCCCC*GTCGAC* GCCGCCACCATGAGAATTTCGAAACCACATTTGAG |
| | antisense (SEQ ID NO:5) | ATCGGG*CTCGAG* TCAAGAAGTGTTGATGAACATTTGG |
| Human IL-15 (SSP) | sense (SEQ ID NO:6) | GCCCCC*GGTACC* GCCGCCACCATGGTATTGGGAACCATA |
| | antisense (SEQ ID NO:7) | ATCGGG*GGATCC* TCAAGAAGTGTTGATGAACAT |
| Legend: *Restriction Site*, KOZAK, START, STOP CODON | | |

FIGURE 10

Strategy for Increasing Expression of IL-15 through Replacement of 48 amino acid Signal Peptide (LSP) with IgE leader ❖ Sense primers are designed to start after 48 aa ISP while antisense primer amplifies from stop site.

❖ Primers are designed to include a strong KOZAK context (GCCGCCACC).
- ❖Sense primer is designed to contain the sequence for IgE leader sequence plus a ATG start site.

| *Primer Name* | *Sense/Antisense* | *Sequence 5' to 3'* |
|---|---|---|
| Human IL-15-IgE | sense (SEQ ID NO: 8) | GCCCCC*GAATTC* GCCGCCACCATGGATTGGACTTGGATCTTATTTTT |
| | (SEQ ID NO: 9) | AGTTGCTGCTGCTACTAGAGTTCATTCTAACTGGGTGAATGTAATAAGT |
| | antisense(SEQ ID NO: 5) | ATCGGG*CTCGAG* TCAAGAAGTGTTGATGAACATTTGG |
| Macaque IL-15-IgE | sense (SEQ ID NO: 8) | GCCCCC*GAATTC* GCCGCCACCATGGATTGGACTTGGATCTTATTTTT |
| | (SEQ ID NO: 9) | AGTTGCTGCTGCTACTAGAGTTCATTCTAACTGGGTGAATGTAATAAGT |
| | antisense(SEQ ID NO: 5) | ATCGGG*CTCGAG* TCAAGAAGTGTTGATGAACATTTGG |

Legend: *Restriction Site*, KOZAK, START, STOP CODON

FIGURE 11

SEQUENCE LISTING

<160> NUMBER OF SEQ ID NOS: 9

<210> SEQ ID NO 1
<211> LENGTH: 14
<212> TYPE: PRT
<213> ORGANISM: Artificial Sequence
<220> FEATURE:
<223> OTHER INFORMATION: chemically synthsized peptide

<400> SEQUENCE: 1

Ala Met Gln Met Leu Lys Glu Thr Met Glu Glu Ala Ala Glu
1               5                   10

<210> SEQ ID NO 2
<211> LENGTH: 9
<212> TYPE: PRT
<213> ORGANISM: Artificial Sequence
<220> FEATURE:
<223> OTHER INFORMATION: chemically synthsized peptide

<400> SEQUENCE: 2

Ala Met Gln Met Leu Lys Glu Thr Ile
1               5

<210> SEQ ID NO 3
<211> LENGTH: 13
<212> TYPE: PRT
<213> ORGANISM: Artificial Sequence
<220> FEATURE:
<223> OTHER INFORMATION: chemically synthesized peptide

<400> SEQUENCE: 3

Phe Arg Asp Val Asp Arg Phe Tyr Lys Thr Arg Ala Glu
1               5                   10

<210> SEQ ID NO 4
<211> LENGTH: 47
<212> TYPE: DNA
<213> ORGANISM: Artificial Sequence
<220> FEATURE:
<223> OTHER INFORMATION: oligonucleotide primer

<400> SEQUENCE: 4
gcccccgtcg acgccgccac catgagaatt tcgaaaccac atttgag            47

<210> SEQ ID NO 5
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 5

```
atcgggctcg agtcaagaag tgttgatgaa catttgg                            37

<210> SEQ ID NO 6
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 6
gcccccggta ccgccgccac catggtattg ggaaccata                          39

<210> SEQ ID NO 7
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 7 atcggggat cctcaagaag tgttgatgaa cat                                 33

<210> SEQ ID NO 8
<211> LENGTH: 47
<212> TYPE: DNA
<213> ORGANISM: Artificial Sequence
<220> FEATURE:
<223> OTHER INFORMATION: oligonucleotide primer

<400> SEQUENCE: 8
gcccccgaat tcgccgccac catggattgg acttggatct tattttt                 47

<210> SEQ ID NO 9
<211> LENGTH: 49
<212> TYPE: DNA
<213> ORGANISM: Artificial Sequence
<220> FEATURE:
<223> OTHER INFORMATION: oligonucleotide primer

<400> SEQUENCE: 9
agttgctgct gctactagag ttcattctaa ctgggtgaat gtaataagt               49
```

NUCLEIC ACID SEQUENCES ENCODING AND COMPOSITIONS COMPRISING IGE SIGNAL PEPTIDE AND/OR IL-15 AND METHODS FOR USING THE SAME

CROSS-REFERENCE TO RELATED APPLICATIONS

This application is a national stage application of PCT International Application PCT/US2004/018962, filed Jun. 14, 2004, which claims priority to U.S. Provisional Patent Applications 60/478,205, filed Jun. 13, 2003; and 60/478,210, filed Jun. 13, 2003.

FIELD OF THE INVENTION

The present invention relates to improved vaccines, improved methods for prophylactically and/or therapeutically immunizing individuals against immunogens, and to improved immunotherapeutic compositions and improved immunotherapy methods.

IN THE SEQUENCE LISTING

Background of the Invention

Immunotherapy refers to modulating a person's immune responses to impart a desirable therapeutic effect. Immunotherapeutics refer to those compositions which, when administered to an individual, modulate the individual's immune system sufficient to ultimately decrease symptoms which are associated with undesirable immune responses or to ultimately alleviate symptoms by increasing desirable immune responses. In some cases, immunotherapy is part of a vaccination protocol in which the individual is administered a vaccine that exposes the individual to an immunogen against which the individual generates an immune response. in such cases, the immunotherapeutic increases the immune response and/or selectively enhances a portion of the immune response (such as the cellular arm or the humoral arm) which is desirable to treat or prevent the particular condition, infection or disease.

Vaccines are useful to immunize individuals against target antigens such as allergens, pathogen antigens or antigens associated with cells involved in human diseases. Antigens associated with cells involved in human diseases include cancer-associated tumor antigens and antigens associated with cells involved in autoimmune diseases.

In designing such vaccines, it has been recognized that vaccines that produce the target antigen in cells of the vaccinated individual are effective in inducing the cellular arm of the immune system. Specifically, live attenuated vaccines, recombinant vaccines which use avirulent vectors, and DNA vaccines each lead to the production of antigens in the cell of the vaccinated individual which results in induction of the cellular arm of the immune system On the other hand, killed or inactivated vaccines, and sub-unit vaccines which comprise only proteins do not induce good cellular immune responses although they do induce a humoral response.

A cellular immune response is often necessary to provide protection against pathogen infection and to provide effective immune-mediated therapy for treatment of pathogen infection, cancer or autoimmune diseases. Accordingly, vaccines that produce the target antigen in cells of the vaccinated individual such as live attenuated vaccines, recombinant vaccines that use avirulent vectors and DNA vaccines are often preferred.

While such vaccines are often effective to immunize individuals prophylactically or therapeutically against pathogen infection or human diseases, there is a need for improved vaccines. There is a need for compositions and methods that produce an enhanced immune response.

Likewise, while some immunotherapeutics are useful to modulate immune response in a patient there remains a need for improved immunotherapeutic compositions and methods.

Gene therapy refers to the delivery of genes to an individual who is in need of or can otherwise benefit by the protein encoded by the protein. Numerous strategies have been developed to deliver proteins for which the individual does not have a corresponding gene that produces sufficient and/or fully functional protein. Thus the gene therapy compensates for the lack of sufficient fully functioning endogenous protein. In some gene therapy strategy, the patient is provided with a therapeutically effective protein using constructs designed to produce a therapeutically effective amount of the protein. The gene therapy provides an alternative method for delivering protein therapeutics. There remains a need for improved gene therapy compositions and methods.

In addition to direct administration of nucleic acid molecules to individuals, proteins are often delivered. Production of such proteins by recombinant methods is often the most efficient way to manufacturing them. There remains a need for improved protein manufacturing compositions and methods.

SUMMARY OF THE INVENTION

The present invention relates to recombinant vaccines that comprise a nucleic acid molecule that comprises a nucleic acid sequence that encodes an immunogen and a nucleic acid sequence that encodes a fusion protein that comprises a non-IL-15 signal sequence linked to IL-15 protein sequences and optionally, a nucleic acid sequence that encodes CD40L; and to methods of immunizing an individual against an immunogen comprising administering to an individual such recombinant vaccines.

The present invention relates to live attenuated pathogens that comprise a nucleic acid molecule that comprises a nucleic acid sequence that encodes a fusion protein that comprises a non-IL-15 signal sequence linked to IL-15 protein sequences and optionally, a nucleic acid sequence that encodes CD40L; to methods of immunizing an individual; and to methods of immunizing an individual against a pathogen comprising administering to an individual such live attenuated pathogens.

The present invention relates to isolated nucleic acid molecules that comprises nucleic acid sequence that encodes IL-15 protein and a nucleic acid sequence that encodes CD40L protein, and optionally, a nucleic acid sequence that encodes an immunogen.

The present invention relates to compositions that comprise a nucleic acid molecule that comprises a nucleic acid sequence that encodes IL-15 protein and a nucleic acid molecule that comprises a nucleic acid sequence that encodes CD40L protein, and optionally, on either or both nucleic acid molecules a nucleic acid sequence that encodes an immunogen.

The present invention relates to methods of modulating an immune response in an individual comprising administering to an individual a composition that comprises one or more nucleic acid molecules that comprise a nucleic acid sequence that IL-15 protein and a nucleic acid sequence that encodes CD40L. The various nucleic acid sequences that encode the various different proteins may be on the same nucleic acid molecule and/or different nucleic acid molecules or both.

The present invention relates to methods of inducing an immune response against an immunogen in an individual that comprises administering to an individual a composition that comprises one or more nucleic acid molecules that comprises a nucleic acid sequence that encodes IL-15 protein, and a nucleic acid sequence that encodes an immunogen and a nucleic acid sequence that encodes CD40L. The various nucleic acid sequences that encode the various different proteins may be on the same nucleic acid molecule and/or different nucleic acid molecules or combinations thereof.

The present invention relates to recombinant vaccines that comprise a nucleic acid molecule that comprises a nucleic acid sequence that encodes an immunogen, a nucleic acid sequence that encodes IL-15 protein, and a nucleic acid sequence that encodes CD40L; and to methods of immunizing an individual against an immunogen comprising administering to an individual such recombinant vaccines.

The present invention relates to live attenuated pathogens that comprise a nucleic acid molecule that comprises a nucleic acid sequence that encodes IL-15 protein and a nucleic acid sequence that encodes CD40L; and to methods of immunizing an individual against a pathogen comprising administering to an individual such live attenuated pathogens.

The present invention relates to nucleic acid molecules that comprise a nucleic acid sequence that encode fusion proteins that consists of an IgE signal peptide linked to non-IgE protein sequences wherein the IgE signal peptide and the non-IgE protein sequences are derived from the same animal species.

The present invention relates to in vitro host cell cultures comprising expression vectors operable in such host cells that comprise a nucleic acid sequence that encode fusion proteins that consists of an IgE signal peptide linked to non-IgE protein sequences; to such nucleic acid molecules; and to host cells comprising such vectors.

The present invention relates to nucleic acid molecules that comprise nucleic acid sequences that encode fusion proteins that comprising an IgE signal peptide linked to non-IgE protein sequences operably linked to regulatory elements required for expression and nucleic acid sequences that encode an immunogen operably linked to regulatory elements required for expression.

The present invention relates to compositions that comprise nucleic acid molecules that comprises nucleic acid sequences that encode fusion proteins that comprising an IgE signal peptide linked to non-IgE protein sequences and nucleic acid molecules that comprise nucleic acid sequences that encode an immunogen, wherein the nucleic acid molecules that comprises nucleic acid sequences that encode the fusion protein are not identical to the nucleic acid molecules that comprise nucleic acid sequences that encode the immunogen.

The present invention relates to isolated fusion proteins that comprise an IgE signal peptide linked to non-IgE protein sequences.

The present invention relates to methods of modulating an immune response in an individual that comprise administering to an individual a composition that comprises a nucleic acid molecule comprising nucleic acid sequences that encode fusion proteins that comprising an IgE signal peptide linked to an immunomodulatory protein.

The present invention relates to methods of inducing an immune response against an immunogen in an individual that comprise administering to an individual nucleic acid molecules that comprise a nucleic acid sequence that encodes a fusion protein that comprises an IgE signal peptide linked to an immunomodulatory protein and a nucleic acid sequence that encodes an immunogen. The various coding sequences for the different proteins may be on the same nucleic acid molecule and/or different nucleic acid molecule.

The present invention relates to recombinant vaccines that comprise a nucleic acid molecule that comprises a nucleic acid sequence that encodes an immunogen and a nucleic acid sequence that encodes a fusion protein comprising an IgE signal sequence linked to an immunomodulatory protein; and to methods of immunizing an individual against an immunogen comprising administering to an individual such recombinant vaccines.

The present invention relates to live attenuated pathogens that comprise a nucleic acid molecule that comprises a nucleic acid sequence that encodes a fusion protein comprising an IgE signal sequence linked to an immunomodulating protein; and to methods of immunizing an individual against an pathogen comprising administering to an individual such live attenuated pathogens.

The present invention relates to nucleic acid molecules that comprise a nucleic acid sequence that encodes a fusion protein that comprises an IgE signal peptide linked to IL-15 protein sequences; to vectors comprising such nucleic acid molecules; and to host cells comprising such vectors.

The present invention relates to fusion proteins that comprise an IgE signal peptide linked to IL-15 protein sequences.

The present invention relates to compositions that comprise a nucleic acid molecule that comprises a nucleic acid sequence that encodes a fusion protein that comprises an IgE signal peptide linked to IL-15 protein sequences, and a nucleic acid molecule that comprises a nucleic acid sequence that encodes an immunogen. Optionally, a nucleic acid sequence that encodes CD40L may be present in nucleic acid molecules that comprise a nucleic acid sequence that encodes the fusion protein and/or the immunogen or in a separate nucleic acid molecule.

The present invention relates to methods of modulating an immune response in an individual comprising administering to an individual a composition that comprises one or more nucleic acid molecules that comprise a nucleic acid sequence that encodes a fusion protein that comprise an IgE signal peptide linked to IL-15 protein, and optionally a nucleic acid sequence that encodes CD40L. The various nucleic acid sequences that encode the various different proteins may be on the same nucleic acid molecule and/or different nucleic acid molecules or both.

The present invention relates to methods of inducing an immune response against an immunogen in an individual that comprises administering to an individual a composition that comprises one or more nucleic acid molecules that comprises a nucleic acid sequence that encodes a fusion protein that comprises an IgE signal peptide linked to IL-15 protein sequences, a nucleic acid sequence that encodes an immunogen and optionally, a nucleic acid sequence that encodes CD40L. The various nucleic acid sequences that encode the various different proteins may be on the same nucleic acid molecule and/or different nucleic acid molecules or combinations thereof.

BRIEF DESCRIPTION OF THE DRAWINGS

In FIG. 4, panel A, the spleenocytes were tested by a standard Chromium release assay for CTL activity against HIV-1 envelope and recombinant vaccinia infected P815 cells. In FIG. 4, panel B, the level of HIV-1 antigen specific chemokine secretion was analyzed. Splenocytes were stimulated with HIV-1 env recombinant vaccinia infected P815 cells. Supernatants were harvested on the third day and tested for secretion of MIP-1β. In FIG. 4, panel C, the level of antigen specific secretion of IFN-gamma was assessed. Splenocytes were resuspended at a concentration of $5 \times 10^6$ cells/ml. A 100 μl aliquot was added to each well of a 96 well microtiter flat bottom plate. Recombinant p24 protein was added to wells in triplicate resulting in the final concentrations of 5 μg/ml and 1 μg/ml. The cells were incubated at 37° C. in 5% $CO_2$ for three days and the supernatants harvested. The level of cytokine secreted were determine using commercially available ELISA kits.

FIG. 5, panel A, shows data for IFN-γ. FIG. 5, panel B, shows data for Tumor Necrosis Factor-α. Dot plots display responses from CD3+/CD8+ lymphocytes.

FIG. 8, panels A, B and C depict data from Example 1 showing production of IFN-γ following stimulation of spleenocytes derived from CD4 knock-out mice. In FIG. 8, panel A, Balb/c mice were co-injected at weeks 0 and 2 with 50 μg of pCgag with 50 μg of the pIL-15, an IL-15 expressing plasmid. Splenocytes were harvested two weeks post the final immunization and tested for HIV-1 specific production of IFN-γ by ELISPOT. In FIG. 8, panel B, $Cd4^{tm1Knw}$ mice were immunized with pCgag with and without pIL-15. In FIG. 8, panel C, $Cd4^{tm1Knw}$ mice were immunized with pCgag in combination with either, pIL-15, pCD40L or both. Splenocytes were harvested two weeks post the final immunization and assayed for HIV-1 Gag specific production of INF-gamma following in vitro stimulation with HIV-1 Gag peptides.

FIG. 10, FIG. 11, FIG. 12 panels A-C, FIGS. 13 panels A-B, 14 and 15 refer to the disclosure set forth in Example 3.

DETAILED DESCRIPTION OF PREFERRED EMBODIMENTS

Definitions

Figure 1:
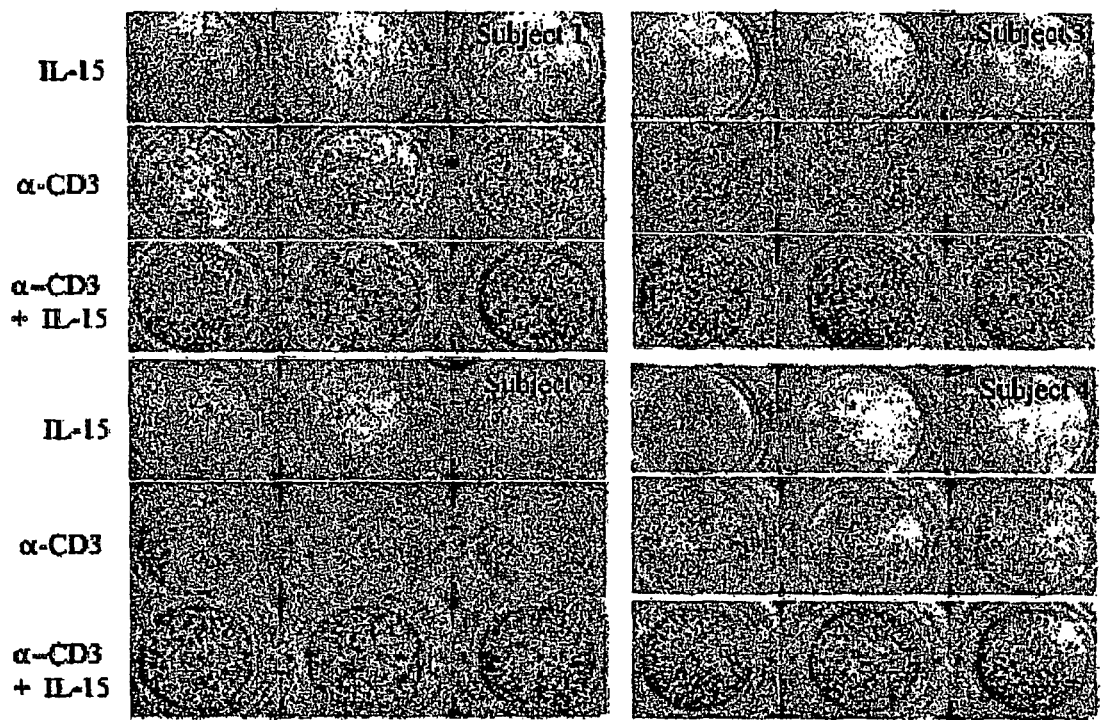
FIG. 1 depicts data from Example 1 showing production of IFN-γ following stimulation of human PBMCs with IL-15 and monoclonal antibody to CD3. PBMCs were obtained from HIV-1 chronically infected subjects being treated with triple therapy (HAART). All donors' viral loads were below 500 copies/ml and their CD4 counts were above 500 cells/ml. To determine if IL-15 enhanced IFN-γ production as an indication of effector function, the cells were stimulated with IL-15 and anti-CD3 and analyzed by a standard ELIspot assay.

As used herein the term "target protein" is meant to refer to peptides and protein encoded by gene constructs of the present invention that act as target proteins for an immune response. The terms "target protein" and "immunogen" are used interchangeably and refer to a protein against which an immune response can be elicited. The target protein is an immunogenic protein that shares at least an epitope with a protein from the pathogen or undesirable cell-type such as a cancer cell or a cell involved in autoimmune disease against which an immune response is desired. The immune response directed against the target protein will protect the individual against and/or treat the individual for the specific infection or disease with which the target protein is associated.

As used herein, the term "genetic construct" refers to the DNA or RNA molecules that comprise a nucleotide sequence that encodes a target protein or immunomodulating protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operable linked to a coding sequence that encodes a target protein or an immunomodulating protein, such that when present in the cell of the individual, the coding sequence will be expressed.

As used herein, the term "sharing an epitope" refers to proteins that comprise at least one epitope that is identical to or substantially similar to an epitope of another protein.

As used herein, the term "substantially similar epitope" is meant to refer to an epitope that has a structure that is not identical to an epitope of a protein but nonetheless invokes a cellular or humoral immune response which cross reacts to that protein.

As used herein, the term "intracellular pathogen" is meant to refer to a virus or pathogenic organism that, at least part of its reproductive or life cycle, exists within a host cell and therein produces or causes to be produced, pathogen proteins.

As used herein, the term "hyperproliferative diseases" is meant to refer to those diseases and disorders characterized by hyperproliferation of cells.

As used herein, the term "hyperproliferative-associated protein" is meant to refer to proteins that are associated with a hyperproliferative disease.

As used herein the term "immunomodulating protein" refers to a protein that modulates the immune system of a person to whom the immunomodulating protein is delivered. Examples of immunomodulatory proteins include: IL-15, CD40L, TRAIL; TRAILrecDRC5, TRAIL-R2, TRAIL-R3, TRAIL-R4, RANK, RANK LIGAND, Ox40, Ox40 LIGAND, NKG2D, F461811 or MICA, MICB, NKG2A, NKG2B, NKG2C, NKG2E, NKG2F, CD30, CD153 (CD30L), Fos, c-jun, Sp-1, Ap1, Ap-2, p38, p65Rel, MyD88, IRAK, TRAF6, IkB, NIK, SAP K, SAP1, JNK2, JNK1B2, JNK1B1, JNK2B2, JNK2B1, JNK1A2, JNK2A1, JNK3A1, JNK3A2, NF-kappa-B2, p49 splice form, NF-kappa-B2, p100 splice form, NF-kappa-B2, p105 splice form, NF-kappa-B 50K chain precursor, NFkB p50, human IL-1α, human IL-2, human IL-4, murine IL-4, human IL-5, human IL-10, human IL-15, human IL-18, human TNF-α, human TNF-β, human interleukin 12, MadCAM-1, NGF IL-7, VEGF, TNF-R, Fas, CD40L, IL-4, CSF, G-CSF, GM-CSF, M-CSF, LFA-3, ICAM-3, ICAM-2, ICAM-1, PECAM, P150.95, Mac-1, LFA-1, CD34, RANTES, IL-8, MIP-1α, E-selecton, CD2, MCP-1, L-selecton, P-selecton, FLT, Apo-1, Fas, TNFR-1, p55, WSL-1, DR3, TRAMP, Apo-3, AIR, LARD, NGRF, DR4 (TRAIL), DR5, KILLER, TRAIL-R2, TRICK2, DR6, ICE, VLA-1, and CD86 (B7.2).

Overview

The invention arises from the following discoveries. 1) IL-15 protein expression levels are higher when the IL-15 signal peptide is not present, whether the IL-15 protein is expressed is a "truncated" IL-15 protein or as a fusion protein comprising the IL-15 protein sequences linked to non-IL-15 signal peptide, particularly IgE signal peptide. IL-15 protein free of the IL-15 signal peptide, whether a "truncated" IL-15 protein or as a fusion protein comprising the IL-15 protein sequences linked to non-IL-15 signal peptide, particularly IgE signal peptide are particularly useful in vaccines and in constructs for delivery of IL-15 protein as an immunomodulating protein. 2) Vaccines and immunomodulatory compositions that involve delivery of IL-15 in combination with CD40L are particularly useful. 3) Fusion proteins that comprise the IgE signal peptide facilitate enhanced expression and are particularly, inter alia, useful in protein production, vaccines and gene therapeutics such as for the delivery of proteins such as immunomodulating proteins. In some preferred embodiments, the invention provides vectors, vaccines and immunomodulatory compositions and methods comprising nucleic acid molecules that comprise nucleotide sequences that encode: proteins including human IL-15 coding sequences free of the IL-15 signal peptide and preferably free of the IL-15 Kozak region and untranslated regions; or fusion proteins in which the human IL-15 coding sequences are provided with a non-IL-15 signal peptide, preferably the IgE signal sequence. IL-15 coding sequences are preferably free of IL-15 signal sequence, and preferably free of the IL-15 Kozak region and untranslated regions. In some preferred embodiments, the invention provides vectors, vaccines and immunomodulatory compositions and methods comprising nucleic acid molecules that comprise nucleotide sequences that encode 1) an IL-15 protein, such as an IL-15 protein free of the IL-15 signal peptide, or a fusion protein that comprises IL-15 protein sequences linked to a non-IL-15 signal peptide such as IgE signal peptide, in combination with 2) nucleotide sequences that encode human CD40L. IL-15 coding sequences are preferably free of IL-15 signal sequence, and preferably free of the IL-15 Kozak region and untranslated regions. In some preferred embodiments, the invention provides vectors, vaccines and immunomodulatory compositions and methods comprising nucleic acid molecules that comprise nucleotide sequences that encode fusion proteins in which the IgE signal peptide is linked to a non-IgE protein sequence, preferably human IL-15 protein sequences.

Fusion Proteins Comprising and Genetic Constructs Encoding IgE Signal Sequence Linked to Non-IgE Protein Thus, one general aspect of the invention relates to fusion proteins comprising and genetic constructs encoding IgE signal sequence linked to non-IgE protein and the use of such constructs in expression vectors, vaccines and immunomodulatory compositions. Several different embodiments and forms are provided with respect to this aspect.

According to some embodiments, compositions are provided which comprise an isolated nucleic acid molecule comprising a nucleic acid sequence that encodes a fusion protein comprising an IgE signal sequence operable linked to non-IgE protein sequence.

The nature of the non-IgE protein is dependent upon the intended use of the constructs. For example, for gene therapy embodiments, the protein sequences would be those of a desired protein such as a protein for which patient lacks sufficient amounts of a functioning or fully functioning protein. Examples of this type of desired protein include enzymes such as DNAse, growth factors such as growth hormone (human, bovine, porcine), clotting factors, insulin, dystrophin, and the like. The desired protein may also be one that when expressed in the patient provides a therapeutic benefit such as erythropoeitin, IL-2, GM-CSF, TPA, and the like. In some embodiments, the non-IgE protein sequence is an immunogen. Such constructs are useful in vaccines in which expression of the immunogen is provided as a target for an immune response. In some embodiments, the non-IgE protein sequence is an immunomodulating protein. Such constructs are useful in vaccines in which expression of the immunogen is provided as a target for an immune response as well as immunomodulatory compositions in which the desired effect is to have the immune system of a patient, or a specific aspect of the immune system upregulated or downregulated depending upon the condition of the patient being treated. Immunomodulators that upregulate the immune system are useful to treat patients suffering immunosuppression or infectious diseases for example while those that downregulate the immune system are useful for example to treat autoimmune diseases, patients receiving organ transplants, tissue grafts or cell therapy for whom immune suppression is desirable. In some embodiment, the IgE signal sequence is linked to a non-IgE protein sequence for use in a system in which production of the IgE protein is desirable. In preferred embodiments, the IgE signal peptide is derived as from the same species of animal as the protein sequences to which it is linked. In preferred methods, the animal being administered such constructs is the same species as the animal from which the IgE signal peptide and protein sequence are derived. Such fusion proteins would be considered to be non-immunogenic.

In some embodiments, compositions that include a construct which comprise coding sequences of IgE signal linked to non-IgE protein sequence that are immunomodulating protein may also include on the same nucleic acid molecule or a different nucleic acid molecule, a nucleic acid sequence that encodes an immunogen. Generally, immunogens, which are discussed below, may be any immunogenic protein including allergens, pathogen antigens, cancer-associated antigens or antigens linked to cells associated with autoimmune diseases. In preferred embodiments, the immunogen is a pathogen antigen, most preferably a pathogen selected from the group consisting of HIV, HSV, HCV, and WNV.

As noted above, the non-IgE protein sequence is preferably an IL-15 protein, more preferably an IL-15 protein free of IL-15 signal sequence, more preferably more preferably an IL-15 protein free of IL-15 signal sequence, free of IL-15 Kozak region and free of IL-15 untranslated sequences. In some preferred embodiments, such compositions further comprise a nucleotide sequence that encodes CD40L. This nucleotide sequence may be included on the same nucleic acid molecule as the fusion protein or a different molecule. The CD40L may be included in vaccine compositions that include coding sequences for immunogens, yielding improved vaccines. In other embodiments, the CD40L may be included in immunomodulatory compositions that do not include coding sequences for immunogens, yielding improved immunomodulatory compositions.

In some preferred embodiments, nucleic acid constructs are plasmids. In some preferred embodiments, the nucleic acid molecule is incorporated in a viral vector such as vaccinia, adenovirus, adenovirus associated virus, retrovirus, or any other acceptable viral vector useful as a vaccine or gene therapy vector.

Genetic constructs comprising IgE signal sequences linked to non-IgE protein sequence that are immunomodulating proteins may be incorporated directly into live attenuated pathogens according to some aspect of the invention. Examples of such pathogens useful as vaccines are set out below. In preferred embodiments, the immunomodulating protein is IL-15, more preferably IL-15 protein free of IL-15 signal sequence, more preferably IL-15 protein free of IL-15 signal sequence free of IL-15 Kozak region and free of IL-15 untranslated sequences. In some embodiments, such attenuated pathogens are further provided with a nucleotide sequence that encodes CD40L.

A fusion protein that comprise an IgE signal sequence operable linked to non-IgE protein sequences are also aspects of the invention. In some embodiments, the non-IgE protein sequence portion of the fusion protein is an enzyme. In some embodiments, the non-IgE protein sequence portion of the fusion protein is an immunogen. In some embodiments, the non-IgE protein sequence portion of the fusion protein is an immunomodulating protein. The preferred non-IgE protein sequence is IL-15 protein, most preferably free of IL-15 signal sequence.

Fusion Proteins Comprising and Genetic Constructs Encoding a Non-IL-15 Signal Sequence Linked to IL-15 Protein One general aspect of the invention relates to fusion proteins comprising and genetic constructs encoding a non-IL-15 signal sequence linked to IL-15 protein and the use of such constructs in vaccines and immunomodulatory compositions. Several different embodiments and forms are provided with respect to this aspect. Generally, IL-15 refers to human IL-15. However, constructs can also refer to IL-15 from other species such as canine, feline, equine, bovine, porcine or ovine for example.

This aspect of the invention arises from the observation that sequences in the protein expressed by the native IL-15 mRNA contain signals or elements which inhibit expression. By removing these inhibitory elements, improved expression is achieved. In preferred embodiments, the IL-15 coding sequence is free of the coding sequence for IL-15 signal peptide, and preferably another signal protein such as IgE signal protein is provided in its place. Moreover, the IL-15 Kozak region and untranslated regions are removed as well to eliminate inhibitory elements. The only Il-15 sequences that constructs preferably include are the IL-15 sequences that encode the amino acid sequence of the mature IL-15 protein free of IL-15 signal peptide.

According to some embodiments, compositions are provided which comprise an isolated nucleic acid molecule comprising a nucleic acid sequence that encodes a fusion protein comprising a non-IL-15 signal sequence linked to IL-15 protein. In some preferred embodiments, a fusion protein consists of a non-IL-15 signal sequence linked to IL-15 protein. In some preferred embodiments, the IL-15 protein is free of IL-15 signal sequence. In some preferred embodiments, the fusion protein is non-immunogenic relative to the species from which the IL-15 sequences are derived. Thus a non-immunogenic fusion protein that comprises human IL-15 would be non-immunogenic in a human.

According to some embodiments, compositions are provided that include a construct which comprises coding sequences for a fusion protein comprising a non-IL-15 signal sequence linked to IL-15 protein may also include on the same nucleic acid molecule or a different nucleic acid molecule, a nucleic acid sequence that encodes an immunogen. Generally, immunogens, which are discussed below, may be any immunogenic protein including allergens, pathogen antigens, cancer-associated antigens or antigens linked to cells associated with autoimmune diseases. In preferred embodiments, the immunogen is a pathogen antigen, most preferably a pathogen selected from the group consisting of HIV, HSV, HCV, and WNV.

In preferred embodiments, the composition further comprises a nucleotide sequence that encodes CD40L. This nucleotide sequence may be included on the same nucleic acid molecule as the fusion protein or a different molecule. The CD40L may be included in vaccine compositions that include coding sequences for immunogens, yielding improved vaccines. In other embodiments, the CD40L may be included in immunomodulatory compositions that do not include coding sequences for immunogens, yielding improved immunomodulatory compositions.

In some preferred embodiments, nucleic acid constructs are plasmids. In some preferred embodiments, the nucleic acid molecule is incorporated in a viral vector such as vaccinia, adenovirus, adenovirus associated virus, retrovirus, or any other acceptable viral vector useful as a vaccine or gene therapy vector.

Genetic constructs comprising nucleotide sequences that encode a fusion protein comprising a non-IL-15 signal sequence linked to IL-15 protein may be incorporated directly into live attenuated pathogens according to some aspect of the invention. Examples of such pathogens useful as vaccines are set out below. In preferred embodiments, human IL-15, preferably free of IL-15 signal sequence, is linked to human IgE signal sequence. In some embodiments, such attenuated pathogens are further provided with a nucleotide sequence that encodes CD40L.

A fusion protein that comprises a non-IL-15 signal sequence linked to IL-15 protein sequence is an aspect of the invention. In some preferred embodiments, a fusion protein consists of a non-IL-15 signal sequence linked to IL-15 protein. In some preferred embodiments, the IL-15 protein is free of IL-15 signal sequence. In some preferred embodiments, the signal sequence is an IgE signal sequence. Sequences are preferably human. In some preferred embodiments, the fusion protein is non-immunogenic. Non-immunogenic refers to the protein being non-immunogenic relative to the species from which the IL-15 sequences are derived.

Compositions Comprising Genetic Constructs Encoding IL-15 and CD40L and Methods of Using the Same Another general aspect of the invention relates to compositions comprising genetic constructs encoding IL-15 and CD40L and the use of such constructs in vaccines and immunomodulatory compositions. Several different embodiments and forms are provided with respect to this aspect. Generally, IL-15 refers to human IL-15. However, constructs can also refer to IL-15 from other species such as canine, feline, equine, bovine, porcine or ovine for example. The IL-15 may be in native form, i.e. with the IL-15 signal sequence. Preferably, the IL-15 is part of a fusion protein that includes a non-Il-15 signal sequence and most preferably is further free of L-15 signal sequence. In preferred embodiments, the IL-15 is linked to an IgE signal sequence.

According to some embodiments, compositions are provided which comprise an isolated nucleic acid molecule comprising a nucleic acid sequence that encodes IL-15 and CD40L or two different isolated nucleic acid molecule including a first that comprises a nucleic acid sequence that encodes IL-15 and a second that comprises a nucleic acid sequence that encodes CD40L. In some preferred embodiments, the protein comprising IL-15 is non-immunogenic relative to the species from which the IL-15 sequences are derived.

According to some embodiments, compositions are provided that include a construct which comprises coding sequences for IL-15 and CD40L may also include on the same nucleic acid molecule or a different nucleic acid molecule, a nucleic acid sequence that encodes an immunogen. Generally, immunogens, which are discussed below, may be any immunogenic protein including allergens, pathogen antigens, cancer-associated antigens or antigens linked to cells associated with autoimmune diseases. In preferred embodiments, the immunogen is a pathogen antigen, most preferably a pathogen selected from the group consisting of HIV, HSV, HCV, and WNV.

Compositions that include coding sequences for immunogens are useful as vaccines. Compositions that do not include coding sequences for immunogens may be useful as immunomodulatory compositions. In some embodiments, protein immunogens, are also provided as a target for the immune response enhanced by the combination IL-15 and CD40L.

In some preferred embodiments, nucleic acid constructs are plasmids. In some preferred embodiments, the nucleic acid molecule is incorporated in a viral vector such as vaccinia, adenovirus, adenovirus associated virus, retrovirus, or any other acceptable viral vector useful as a vaccine or gene therapy vector.

Genetic constructs comprising nucleotide sequences that encode IL-15 and CD40L may be incorporated directly into live attenuated pathogens according to some aspects of the invention. Examples of such pathogens useful as vaccines are set out below. In preferred embodiments, human IL-15, preferably free of IL-15 signal sequence, is linked to human IgE signal sequence Vaccines and Immunomodulatory Compositions According to some embodiments of the invention, compositions of the invention comprise genetic constructs including coding sequences for immunogens and/or immunogenic proteins. Such compositions are delivered to an individual to modulate the activity of the individual's immune system and thereby enhance the immune response against the immunogen. When the nucleic acid molecules that encode an immunomodulatory protein are taken up by cells of the individual the nucleotide sequences that encode the immunomodulatory protein are expressed in the cells and the proteins are thereby delivered to the individual. Aspects of the invention provide methods of delivering the coding sequences of the proteins on a single nucleic acid molecule, in compositions comprising different nucleic acid molecules that encodes one or more of the various transcription factor or intermediate factors, as part of recombinant vaccines and as part of attenuated vaccines.

According to some aspects of the present invention, compositions and methods are provided which prophylactically and/or therapeutically immunize an individual against a pathogen or abnormal, disease-related cells. The vaccine may be any type of vaccine such as, a live attenuated vaccine, a cell vaccine, a recombinant vaccine or a nucleic, acid or DNA vaccine.

The present invention relates to compositions for delivering the immunomodulating proteins and methods of using the same.

The nucleic acid molecules may be delivered using any of several well known technologies including DNA injection (also referred to as DNA vaccination), recombinant vectors such as recombinant adenovirus, recombinant adenovirus associated virus and recombinant vaccinia.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include to mucosal tissue, intramuscular, intraperitoneal, intradermal and subcutaneous injection. Genetic constructs may be administered by means including, but not limited to, traditional syringes, needleless injection devices, or "microprojectile bombardment gene guns".

When taken up by a cell, the genetic construct(s) may remain present in the cell as a functioning extracbromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode a target protein, the immunomodulating protein and, additionally, genes for proteins which further enhance the immune response against such target proteins. Examples of such genes are those which encode other cytokines and lymphokines such as alpha-interferon, gamma-interferon, platelet derived growth factor (PDGF), TNF, GM-CSF, epidermal growth factor (EGF), IL-1, IL-2, II-4, IL-6, IL-10, IL-12 and IL-15 including IL-15 having the signal sequence deleted and optionally including the signal sequence from IgE.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

One method of the present invention comprises the steps of administering nucleic acid molecules intramuscularly, intranasally, intraperatoneally, subcutaneously, intradermally, or topically or by lavage to mucosal tissue selected from the group consisting of inhalation, vaginal, rectal, urethral, buccal and sublingual.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as a-interferon, gamma-interferon, GM-CSF, platelet derived growth factor (PDGF), TNF, epidermal growth factor (EGF), ILA, IL-2, IL-4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalene and squalene, and hyaluronic acid may also be used administered in conjunction with the genetic construct In some embodiments, an immunomodulating protein may be used as a GVF. In some embodiments, the nucleic acid molecule is provided in association with PLG to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some embodiments of the invention, methods of inducing immune responses against an immunogen are provided by delivering compositions of the invention to an individual. The vaccine may be a live attenuated vaccine, a cell vaccine, a recombinant vaccine or a nucleic acid or DNA vaccine.

In addition to using expressible forms of immunomodulating protein coding sequence to improve genetic vaccines, the present invention relates to improved attenuated live vaccines and improved vaccines that use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 10 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference. Gene constructs are provided which include the nucleotide sequence that encodes an immunomodulating protein is operably linked to regulatory sequences that can function in the vaccine to effect expression. The gene constructs are incorporated in the attenuated live vaccines and recombinant vaccines to produce improved vaccines according to the invention.

The present invention provides an improved method of immunizing individuals that comprises the step of delivering gene constructs to the cells of individuals as part of vaccine compositions which include are provided which include DNA vaccines, attenuated live vaccines and recombinant vaccines. The gene constructs comprise a nucleotide sequence that encodes an immunomodulating protein and that is operably linked to regulatory sequences that can function in the vaccine to effect expression. The improved vaccines result in an enhanced cellular immune response.

Immunogens

The present invention is useful to elicit enhanced immune responses against a target protein, i.e. proteins specifically associated with pathogens, allergens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

According to some aspects of the present invention, DNA or RNA that encodes a target protein and immunomodulating proteins is introduced into the cells of tissue of an individual where it is expressed, thus producing the encoded proteins. The DNA or RNA sequences encoding the target protein and one or both immunomodulating proteins are linked to regulatory elements necessary for expression in the cells of the individual. Regulatory elements for DNA expression include a promoter and a polyadenylation signal. In addition, other elements, such as a Kozak region, may also be included in the genetic construct.

In some embodiments, expressible forms of sequences that encode the target protein and expressible forms of sequences that encode both immunomodulating proteins are found on the same nucleic acid molecule that is delivered to the individual.

In some embodiments, expressible forms of sequences that encode the target protein occur on a separate nucleic acid molecule from the nucleic acid molecules that contain expressible forms of sequences that encode one or more immunomodulatory proteins. In some embodiments, expressible forms of sequences that encode the target protein and expressible forms of sequences that encode one or more of the immunomodulatory proteins occur on a one nucleic acid molecule that is separate from the nucleic acid molecule that contain expressible forms of sequences that encode one or more of the immunomodulating proteins. Multiple different nucleic acid molecules can be produced and delivered according to the present invention and delivered to the individual. For example, in some embodiments, expressible forms of sequences that encode the target protein occur on separate nucleic acid molecule from the nucleic acid molecules that contain expressible forms of sequences that encode one or more of the two immunomodulating proteins which occur on separate nucleic acid molecule from the nucleic acid molecules that contain expressible forms of sequences that encode one or more immunomodulating proteins. In such cases, all three molecules are delivered to the individual.

The nucleic acid molecule(s) may be provided as plasmid DNA, the nucleic acid molecules of recombinant vectors or as part of the genetic material provided in an attenuated vaccine or cell vaccine. Alternatively, in some embodiments, the target protein and/or wither or both immunomodulating proteins maybe delivered as a protein in addition to the nucleic acid molecules that encode them or instead of the nucleic acid molecules which encode them.

Genetic constructs may comprise a nucleotide sequence that encodes a target protein or an immunomodulating protein operably linked to regulatory elements needed for gene expression. According to the invention, combinations of gone constructs that include one that comprises an expressible form of the nucleotide sequence that encodes a target protein and one that includes an expressible form of the nucleotide sequence that encodes an immunomodulating protein are provided. Incorporation into a living cell of the DNA or RNA molecule(s) that include the combination of gene constructs results in the expression of the DNA or RNA and production of the target protein and one or more immunomodulating proteins. An enhanced immune response against the target protein results.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, listeria and shigella. In addition, the present invention is also useful to immunize an individual against protozoan pathogens that include a stage in the life cycle where they are intracellular pathogens. Table 1 provides a listing of some of the viral families and genera for which vaccines according to the present invention can be made. DNA constructs that comprise DNA sequences that encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

In order to produce a genetic vaccine to protect against pathogen infection, genetic material that encodes immunogenic proteins against which a protective immune response can be mounted must be included in a genetic construct as the coding sequence for the target. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material that encodes many pathogen antigens. For example, several viral genes may be included in a single construct thereby providing multiple targets.

Tables 1 and 2 include lists of some of the pathogenic agents and organisms for which genetic vaccines can be prepared to protect an individual from infection by them. In some preferred embodiments, the methods of immunizing an individual against a pathogen are directed against HIV, HSV, HCV, WNV or HBV.

Another aspect of the present invention provides a method of conferring a protective immune response against hyperproliferating cells that are characteristic in hyperproliferative diseases and to a method of treating individuals suffering from hyperproliferative diseases. Examples of hyperproliferative diseases include all forms of cancer and psoriasis.

It has been discovered that introduction of a genetic construct that includes a nucleotide sequence which encodes—an immunogenic "hyperproliferating cell"—associated protein into the cells of an individual results in the production of those proteins in the vaccinated cells of an individual. To immunize against hyperproliferative diseases, a genetic construct that includes nucleotide sequence that encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides; which comprise at least an epitope found on such proteins. In some cases, a hyperproliferative-associated protein is the product of a mutation of a gene that encodes a protein. The mutated gene encodes a protein that is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins that are found at higher levels in tumor cells including the protein recognized by monoclonal antibody 17-IA and folate binding proteins or PSA.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) that are involved in the disease have been characterized. These TCRs include V$\beta$-3, V$\beta$-14, 20 V$\beta$-17 and Va-17. Thus, vaccination with a DNA construct that encodes at least one of these proteins will elicit an immune response that will target T cells involved in RA. See: Howell, M. D., et al., 1991 *Proc. Nat. Acad. Sci. USA* 88:10921-10925; Piliard, X., et al, 1991 *Science* 253:325-329; Williams, W. V., et al., 1992 *J Clin. Invest.* 90:326-333; each of which is incorporated herein by reference. In MS, several specific variable regions of TCRs that are involved in the disease have been characterized. These TCRs include VfP and Va-10. Thus, vaccination with a DNA construct that encodes at least one of these proteins will elicit an immune response that will target T cells involved in MS. See: Wucherpfennig, K. W., et al., 1990 *Science* 248: 1016-1019; Oksenberg, J. R., et al, 1990 *Nature* 345:344-346; each of which is incorporated herein by reference.

In scleroderma, several specific variable regions of TCRs that are involved in the disease have been characterized. These TCRs include Vβ-6, Vβ-8, Vβ-14 and Va-16, Va-3C, Va-7, Va-14, Va-15, Va-16, Va-28 and Va-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies that bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al 1987 *Sequence of Proteins of Immunological Interest* U.S. Department of Health and Human Services, Bethesda Md., which is incorporated herein by reference. In addition, a general method for cloning functional variable regions from antibodies can be found in Chaudhary, V. K., et al, 1990 *Proc. Natl. Acad Sci. USA* 87:1066, which is incorporated herein by reference.

Recombinant Protein Production

The present invention relates to in vitro host cell cultures comprising expression vectors operable in such host cells that comprise a nucleic acid sequence that encode fusion proteins that consists of an IgE signal peptide linked to non-IgE protein sequences; to such nucleic acid molecules; and to host cells comprising such vectors. The present invention also relates to methods of producing a fusion proteins comprising the step of culturing the host cell. The present invention relates to isolated fusion proteins that comprise an IgE signal peptide linked to non-IgE protein sequences.

The fusion proteins may be produced by routine means using readily available starting materials as described above. Provision of a suitable DNA sequence encoding the desired protein permits the production of the protein using recombinant techniques now known in the art.

One having ordinary skill in the art can, using well known techniques, insert DNA that encodes a fusion protein into a commercially available expression vector for use in well known expression systems. The commercially available plasmid pYES2 (Invitrogen, San Diego, Calif.) may be used for production in *S. cerevisiae* strains of yeast. The commercially available MaxBac™ (Invitrogen, San Diego, Calif.) complete baculovirus expression system may be used for production in insect cells. The commercially available plasmid pcDNA I (Invitrogen, San Diego, Calif.) may be used for production in may be used for production in mammalian cells such as Chinese Hamster Ovary cells. One having ordinary skill in the art can use these commercial expression vectors systems or others to produce fusion protein using routine techniques and readily available starting materials.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., Molecular Cloning a Laboratory Manual, Second Ed. Cold Spring Harbor Press (1989). Thus, the desired proteins can be prepared in both prokaryotic and eukaryotic systems, resulting in a spectrum of processed forms of the protein.

A wide variety of eukaryotic hosts are also now available for production of recombinant foreign proteins. Eukaryotic hosts may be transformed with expression vectors that produce the desired protein directly using the IgE signal peptide.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host that is then cultured and maintained under conditions wherein expression of the foreign gene takes place. The protein of the present invention thus produced is recovered from the culture, either by lysing the cells or preferably from the culture medium as appropriate and known to those in the art.

One having ordinary skill in the art can, using well known techniques, isolate the fusion receptor protein or fragments thereof produced using such expression systems.

EXAMPLES

Example 1

Introduction

The success of combination antiretroviral therapy, to reduce viral load in infected subjects resulted in improved prognosis for many HIV-1 positive individuals. However, a number of laboratories have reported that the established viral reservoir is poorly impacted by combination drug regimens (References 1-3 below). To date no combination therapy approach has resulted in viral clearance and there are significant side effects associated with current therapeutic regimens that ultimately affect patient compliance and impact disease course. Therefore, there is a great need to explore alternative forms of therapy including potential immunotherapeutic approaches for HIV-1. It is believed CD8+ T cell responses are important for controlling HIV-1 infection and in slowing disease progression. Although the exact function of HIV-1 specific CD8+ T cell responses in controlling viral replication has not been completely elucidated, a correlation has been established between long term non-progression in individuals seropositive for HIV-1 and specific CD8+ T cell-mediated cellular responses (References 4-7 below). In addition, a cohort of highly exposed, but HIV negative individuals in Gambia have not demonstrated antibody responses, yet have shown anti-HIV-1 CD8+ T cell immune responses (References 8 and 9 below). Indeed, following HIV-1 infection a robust cellular immune response is induced with a concurrent drop in viral load. Yet, despite the presence of high levels of HIV specific cytotoxic T lymphocytes (CTL), HIV-1 infection is not cleared. This discrepancy between a high CD8 mediated response and continued disease progression is of concern. The inability of the CTLs to clear virus may be due in part to the CTL escape mutants (References 10-14 below), possibly immunopathogenesis of the virus, such as Nef-associated down-regulation of MHC class I or Vpr or Env effects on the host immunity (References 15-18 below). An additional issue is the lack of effective CD4+ T cell help for CD8+ T lymphocytes (References 19 and 20 below). It has been observed that circulating CD8+ cells may have impaired function (Reference 21 below). If HIV-1 immunopathogenesis limits development of an effective CD8 response, then presentation of HIV-1 antigens in the context of anti-retroviral therapy could boost CD8 memory and effector cells in a limited fashion. These events could have a potential impact on disease outcome. However, it may be important to provide help for CD8+ T cell expansion. In this regard, the survival of CD8+ memory T cells was found not to be contingent on continued antigen presentation, (Reference 22 below) but it might rather be dependent on production of specific cytokines in the peripheral environment.

One such cytokine that appears to significantly impact CD8+ T cells is interleukin-15 (IL-15). Waldmann and colleagues first reported that IL-15 is a 15 kDa protein that uses the gamma and beta chains of the IL-2 receptor complex in concert with a unique alpha chain to signal T cells (Reference 23 below). IL-15 manifests anti-apoptotic activity and appears to play a role in stimulating a memory CD8+ T cell phenotype. The role IL-15 plays in HIV-1 infection is being investigated by a number of groups. IL-15 has been demonstrated to reduce apoptosis of lymphocytes isolated from HIV-1 infected subjects (Reference 24 below) and increase activity and proliferation of natural killer cells, (References 25-27 below). IL-15 has also been implicated in B cell proliferation (References 28 and 29 below) of HIV-1 infected subjects and activation of macrophages (Reference 30 below). Importantly, IL-15 also appears to have a direct role on the HIV-1 effector T cell proliferation and interferon-gamma (IFN-gamma) production (References 31 and 32 below). Yet, IL-15, was not able to stimulate IFN-gamma in many subjects tested who were seropositive for HIV-1. The effects of IL-15 on antigen specific CD8+ T cellular immune responses were therefore explores.

The effects of IL-15 on T cells isolated from chronically infected HIV-1 seropositive subjects were examined. It was found that rhIL-15 enhances proliferation of CD8 T cells, and importantly, IL-15 expanded effector antigen specific CD8+ IFN-gamma production in all subjects. In an immunization model IL-15 boosted CD8+ effector function, which was explored in an immunization model system. CD8+ lymphocytes from mice were able to lyse targets expressing HIV-1 antigens at a higher level when IL-15 was provided in trans. This effect occurred in the absence of strong proliferation of CD4+ T cell. However, in CD4 knockout (KO) mice IL-15 could not completely by-pass the requirement for CD4 help in the generation of the CD8 effector response. These results suggest that IL-15 is highly effective at expansion of CD8 memory cells but IL-15 alone is not sufficient for their initial generation.

Materials and Methods
ELIspot Assay on Human PBMCs

PBMCs isolated from HIV-1 positive volunteers by basic ficoll-hypaque technique were assessed for effector function by a standard ELIspot assay. PBMCs were resuspended in RPMI with 10% FCS (R10) at a concentration of $1 \times 10^6$ cells/ml. The antibody 1-DIK (Mabtech, Mariemont Ohio; Nacka, SE) was diluted to 15 ug/ml in 0.1 M carbonate-bicarbonate solution (pH 9.6) and used to coat 96-well nitrocellulose membrane plates (Millipore, Bedford, Mass.). The plates were incubated at 4° C. overnight. Plates were washed 6 times with 200 µl of PBS. A mixture of 122 sterile peptides was prepared as a cocktail at a concentration (for each peptide) of 50 µg/µl in DMSO. The peptides are a series of overlapping peptides, 15 amino acids in length, that encompass all of HIV-1 Gag (AIDS Reagent and Reference Repository, ARRR). 100,000 PBMCs were added to each well (100 µl @ $1.0 \times 10^6$ cells/ml) of the nitrocellulose antibody-coated plates, along with 100 ul of the peptide cocktail diluted 1:200 in R10 with or without 50 ng/ml IL-15 (final concentration 25 ng/ml). Each sample was assayed in triplicate. PHA at 5 µg/ml was used as a positive control. The plates were incubated at 37° C. for approximately 24 hours. The plates were then washed 6 times with 200 µl of PBS. 100 ul of antibody 7-B6-1-Biotin (Mabtech) was added to each well at a concentration of 1 µg/ml in PBS. Plates were incubated at room temperature for 2-4 hours. The plates were washed 6 times with 200 µl of PBS. 100 µl of Streptavidin-ALP (Mabtech) was added to each well at a concentration of 1 µg/ml in PBS. The plates were incubated at room temperature for 1-2 hours. The plates were washed 6 times with 200 µl of PBS. 100 µl of substrate solution (BCIP/NBT, Sigma) was added to each well. The developing solution was removed with tap water. Dynabeads (Dynal Biotech, Lake success, N.Y.; Oslo, NO) coupled to monoclonal antibody specific for either CD8 or CD4 were used to deplete CD8 and CD4 populations.

Co-Stimulation of PBMCs with Monoclonal Antibody to CD3

Isolated PBMCs from subjects seropositive for HIV-1 were stimulated with monoclonal antibody specific for CD3 bound to Dynabeads (Dynal Biotech) with or without IL-15 (50 ng/ml) and analyzed for production of IFN-gamma by ELISPOT as described above. Dynabeads (Dynal Biotech) coupled to monoclonal antibody specific for either CD8 or CD4 were used to deplete CD8 and CD4 populations.

Co-Stimulation of PBMCs with CD40L

CD40L protein was tested in combination with IL-15 and the peptide mix at a concentration of 250 µg/ml and analyzed for production of IFN-gamma by ELISPOT as described above Plasmid Immunization in Mice Female Balb/c mice were co-vaccinated at weeks 0 and 2 with 50 µg of pCgag or pCenv and 50 µg of the plasmids that express genes of IL-2R-dependent Th1 cytokine IL-15 as previously described (Reference 33 below). Mice homozygous for the $Cd4^{tm1Knw}$ targeted mutation were also used. These mice have a complete block in $CD4^+$ T-cell development due to a mutation in the CD4 gene; 90% of their circulating T-cells are $CD8^+$. Homozygous mutant mice also show a Class II restricted deficit in helper T-cell activity and other T-cell responses. B6.129S6-Cd4$^{tm1Knw}$ were co-vaccinated at weeks 0 and 2 with 50 μg of pCgag and 50 μg of the plasmids that expresses CD40L, IL-15 or both in combination. All DNA was made using Qiagen columns and final formulations were 0.25% bupivacaine in isotonic citrate buffer. Spleens were harvested one week post the second injection.

Murine Cytotoxic T Lymphocyte Assay

The CTL response was assessed in a five hour $^{51}$Cr release CTL assay using recombinant vaccinia infected cells as targets. Splenocytes were isolated one week following vaccination and stimulated in vitro. The effectors were stimulated with relevant vaccinia-infected cells. P815 were infected with vDK1 for gag/pol, (ARRR) or vMN462 (ARRR) for env. The stimulators were fixed with 0.1% glutaraldehyde as previously described and incubated with the splenocytes at a ratio of 1:20 for four to five days in CTL culture media. CTL culture media consisted of 1:1 ratio of Iscove's Modified Dulbecco Media (Gibc—BRL, Grand Island, N.Y.) and Hanks' Balanced Salt Solution (Gibco-BRL) with 10% fetal calf serum 1640 (Gibco-BRL) and 10% RAT-T-STIM without Con A (Becton Dickinson Labware, Bedford, Mass.). Vaccinia-infected targets were prepared by infecting 3×10$^6$ P815 cells at a multiplicity of infection (MOI) of 10 for twelve hours at 37° C. A standard Chromium release assay was performed in which the target cells were labeled with 20 μCi/ml Na$_2$$^{51}$CrO$_4$ for 120 minutes and incubated with the stimulated effector splenocytes for six hours at 37° C. CTL lysis was determined at effector: target (E:T) ratios ranging from 50:1 to 12.5:1. Supernatants were harvested and counted on a LKB CliniGamma gamma-counter. Percent specific lysis is determined from the formula:

$$100 \times \left\{ \frac{\text{experimental release} - \text{spontaneous release}}{\text{maximum release} - \text{spontaneous release}} \right\}$$

Maximum release was determined by lysis of target cells in 1% Triton X-100 containing medium. An assay was not considered valid if the value for the 'spontaneous release' counts was in excess of 20% of the 'maximum release'.

Complement Lysis of CD8+ T Cells

CD8+ T cells were removed from the splenocytes by a treatment with anti-CD8 monoclonal antibody (Pharmingen, San Diego, Calif.) followed by incubation with rabbit complement (Sigma) for 45 min. at 37° C. as described (Reference 33 below).

Murine T Helper Cell Proliferation Assay

A lymphocyte proliferation assay was used to assess the overall immunocompetence of lymphocytes and detect antigen specific dividing cells. Lymphocytes were harvested from spleens and prepared by removing the erythrocytes and washing several times with fresh media as described (Reference 34 below). The isolated cells were resuspended at a concentration of 5×10$^6$ cells/ml. A 100 μl aliquot containing 5×10$^5$ cells was immediately added to each well of a 96 well microtiter flat bottom plate. Recombinant p24 protein was added to wells in triplicate resulting in the final concentration of 5 μg/ml and 1 μg/ml. The cells were incubated at 37° C. in 5% C0$_2$ for three days. One μCi of tritiated thymidine was added to each well and the cells incubated for 12 to 18 hours at 37° C. Plates were harvested and the amount of incorporated tritiated thymidine was measured in a Beta Plate reader (Wallac, Turku, Finland). Stimulation Index was determined from the formula:

Stimulation Index (SI)=(experimental count/spontaneous count)

Spontaneous count wells included 10% fetal calf serum, which will serve as irrelevant protein control. Similarly, spleenocytes from pCgag or control immunized mice routinely have an SI of 1 against their irrelevant protein target. To assure that cells are healthy, PHA or Con A (Sigma) was used as a polyclonal stimulator positive control.

Cytokine and Chemokine Analysis of Stimulated Murine Cells

Lymphocytes were harvested from spleens and the isolated cells were resuspended at a concentration of 5×10$^6$ cells/ml. A 100 μl aliquot containing 5×10$^5$ cells was added to each well of a 96 well microtiter flat bottom plate. Recombinant p24 or envelope protein was added to wells in triplicate resulting in final concentrations of 5 μg/ml and 1 μg/ml. The cells were incubated at 37° C. in 5% C0$_2$ for three days and the supernatants harvested. The cytokines and chemokines were measured with commercially available ELISA kits.

Intracellular Staining for Interferon-γ of Stimulated Murine Cells

Mice were given two injections with either pCgag DNA or pCgag DNA plasmid plus pIL-15. One week later, splenocytes were harvested and cultured in vitro for five hours in media containing a p55 peptide cocktail (containing 122 15mers spanning HIV-1 p55 with 11aa overlaps) and BrefeldinA. After stimulation, cells were stained extracellularly with anti-mouse CD3 and anti-mouse CD8 antibodies and then intracellularly with anti-mouse IFN-γ. Dot plots display responses from CD3+/CD8+ lymophocytes.

Epitope Mapping

Spleenocytes were resuspended in RPMI with 10% FCS (R10) at a concentration of 1×10$^6$ cells/ml. The series of 122 peptides obtained from the AIDS Reference and Reagent Repository were mixed as pools of 10 peptides per pool at a final concentration of 20 μg/ml/peptide. Each peptide was included in two distinct pools for a total of 22 peptide pools. The pools were arranged in a matrix format and used for spleenocyte stimulation. IFN-gamma production was assessed by ELISPOT (R and D Systems). The plates were incubated at 37° C. for approximately 24 hours. Each sample was assayed in triplicate.

Results

Stimulation of Lymphocytes with CD3 and IL-15

Figure 2:
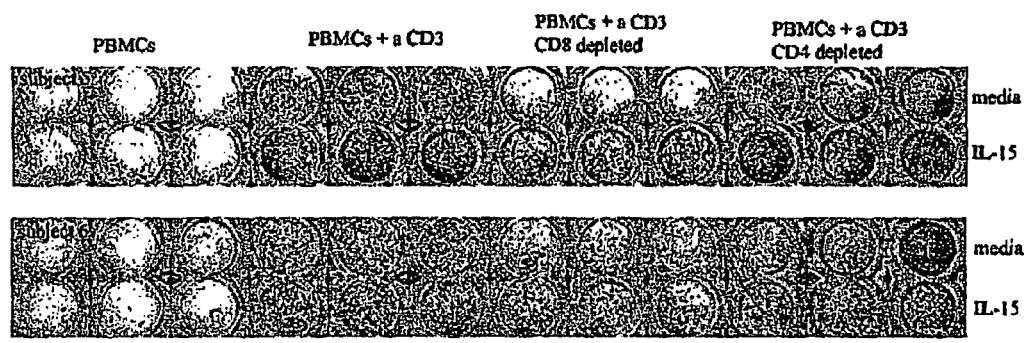
FIG. 2 depicts data from Example 1 showing production of IFN-γ following stimulation of human PBMCs with IL-15 and monoclonal antibody to CD3 is predominantly CD8 mediated. PBMCs from HIV-1 chronically infected subjects being treated with triple therapy (HAART) as described in FIG. 1 were depleted of either CD4 or CD8 T cells and then stimulated with IL-15 and anti-CD3 and analyzed by a standard ELIspot assay.

IL-15 was assessed for its ability to augment T cell effector activation, in a synergistic manner, with T cell receptor stimulation. PBMC's were isolated from HIV-1 infected individuals. PBMCs were stimulated with surface bound antibody to CD3 and then incubated overnight with IL-15. As expected, CD3 stimulation alone of PBMCs induced production of IFN-γ, while IL-15 supplement alone induced low to no response. However, a several fold increase in the number of cells secreting IFN-γ when lymphocytes were stimulated with CD3 and IL-15 together was observed (FIG. 1). The stimulated populations were depleted of CD4+ or CD8+ T cells and then supplemented with IL-15 and again tested for activity. Again, loss of CD8 cells depleted the activation signal. The data indicates that CD8+ effector T cells from chronically infected HIV-1 individuals can be expanded by IL-15/CD3 stimulation (FIG. 2).

Figure 3A:
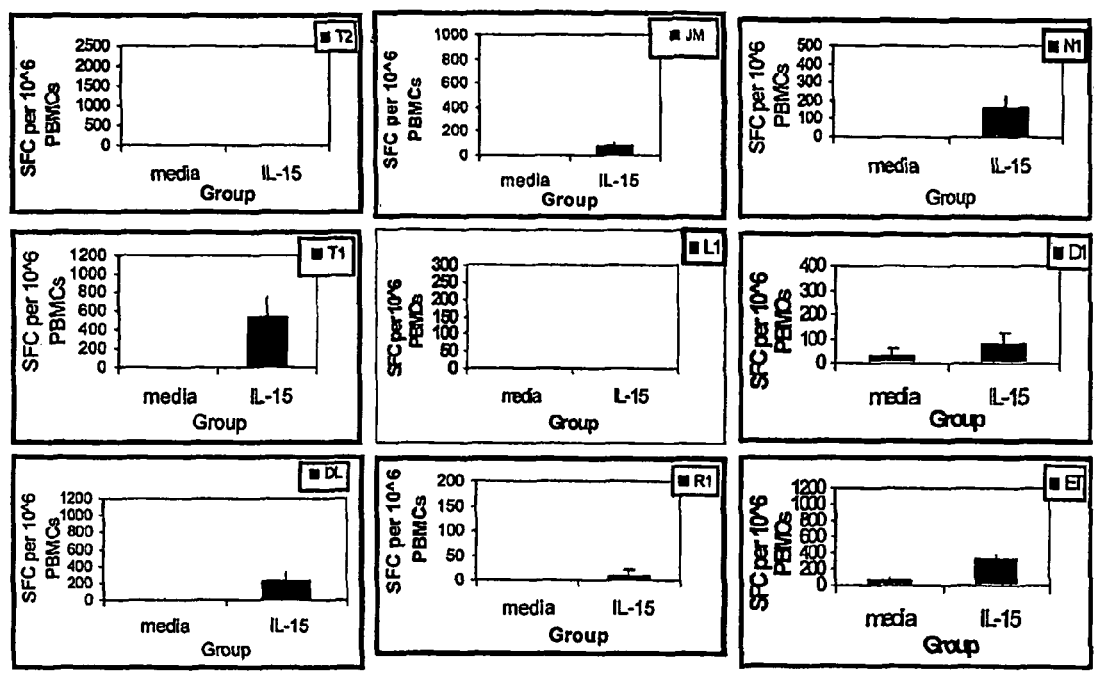
FIGS. 3A, 3B, 3C and 3D depict data from Example 1 showing antigen specific production of IFN-γ following stimulation of human PBMCs with HIV-1 peptides and IL-15. The PBMCs obtained from HIV-1 chronically infected subjects being treated with triple therapy (HAART) were analyzed for their ability to secrete IFN-γ in response to 25 ng/ml of IL-15 (FIGS. 3A and 3C) and to HIV-1 Gag peptides in combination with IL-15 (FIGS. 3B and 3C) in a standard ELIspot assay. CD8 were depleted and the production of IFN-γ following stimulation with HIV-1 peptides and IL-5 was assessed as well (FIG. 3D).
Figure 3B:
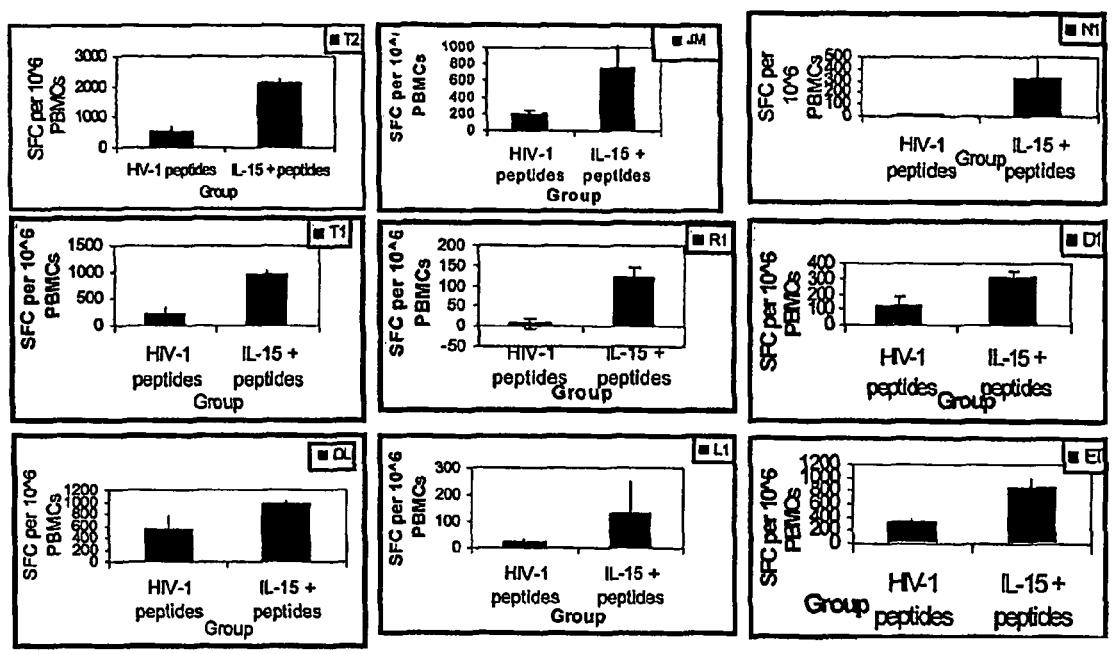
Figure 3C:
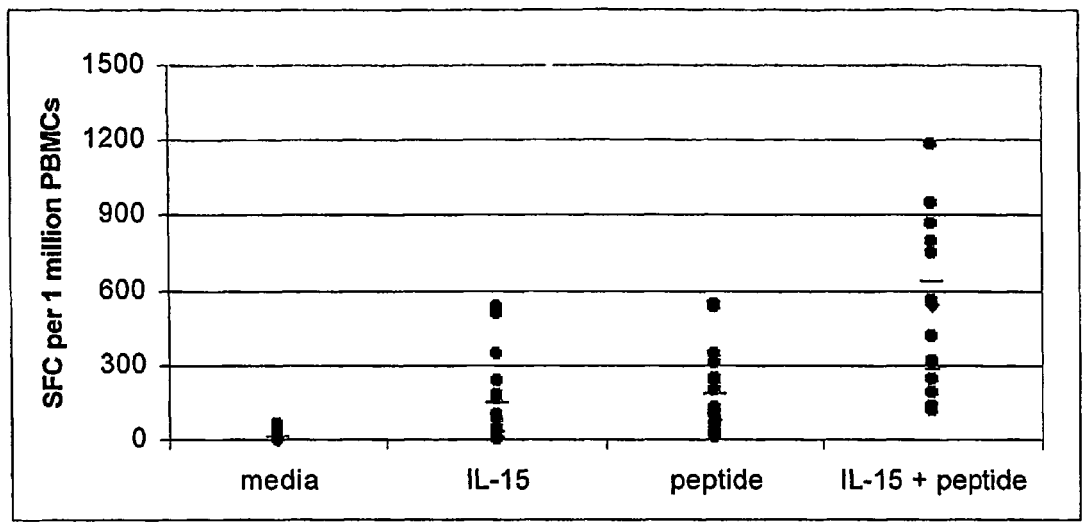
Figure 3D:
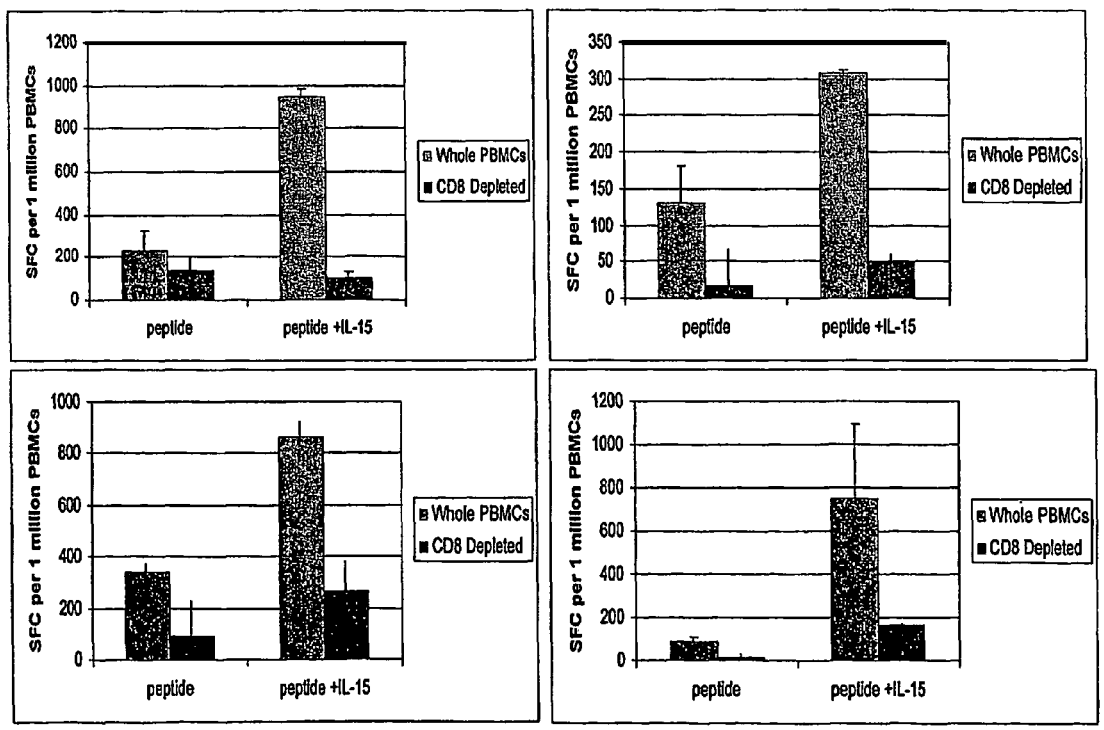

Antigen Specific IFN-7 Production of HIV-1 Positive Samples Following IL-15 Stimulation The ability of IL-15 to enhance an HIV-1 antigen specific CD8+ response was assessed in vitro. Samples were collected from chronically infected HIV-1+ subjects who were being treated with combination anti-retroviral therapy (HAART). PBMCs were assessed for their ability to secrete IFN-gamma following stimulation with HIV-1 specific peptides in the presence or absence of IL-15. PBMCS were stimulated with overlapping HIV-1 15 amino acid peptides that encompassed the entire open reading frame of HIV-1 gag protein. PBMCs from subjects stimulated with peptides exhibited expanded IFN-gamma production when treated with IL-15 (FIGS. 3A and 3B) and there was a significant difference between the IFN-gamma production with and without IL-15 (p=0.009), (FIG. 3C). Some subjects had high levels of INF-gamma secretion with IL-15 stimulation alone (FIG. 3A), suggesting that they had partial T cell activation that was blocked and required cytokine supplement to be effective. This activity was clearly CD8 mediated as IFN-gamma production was lost when the CD8 cell population was depleted (FIG. 3D).

IL-15 Enhances CD8+ CTL Response in Mice In Vivo.

Figure 4:
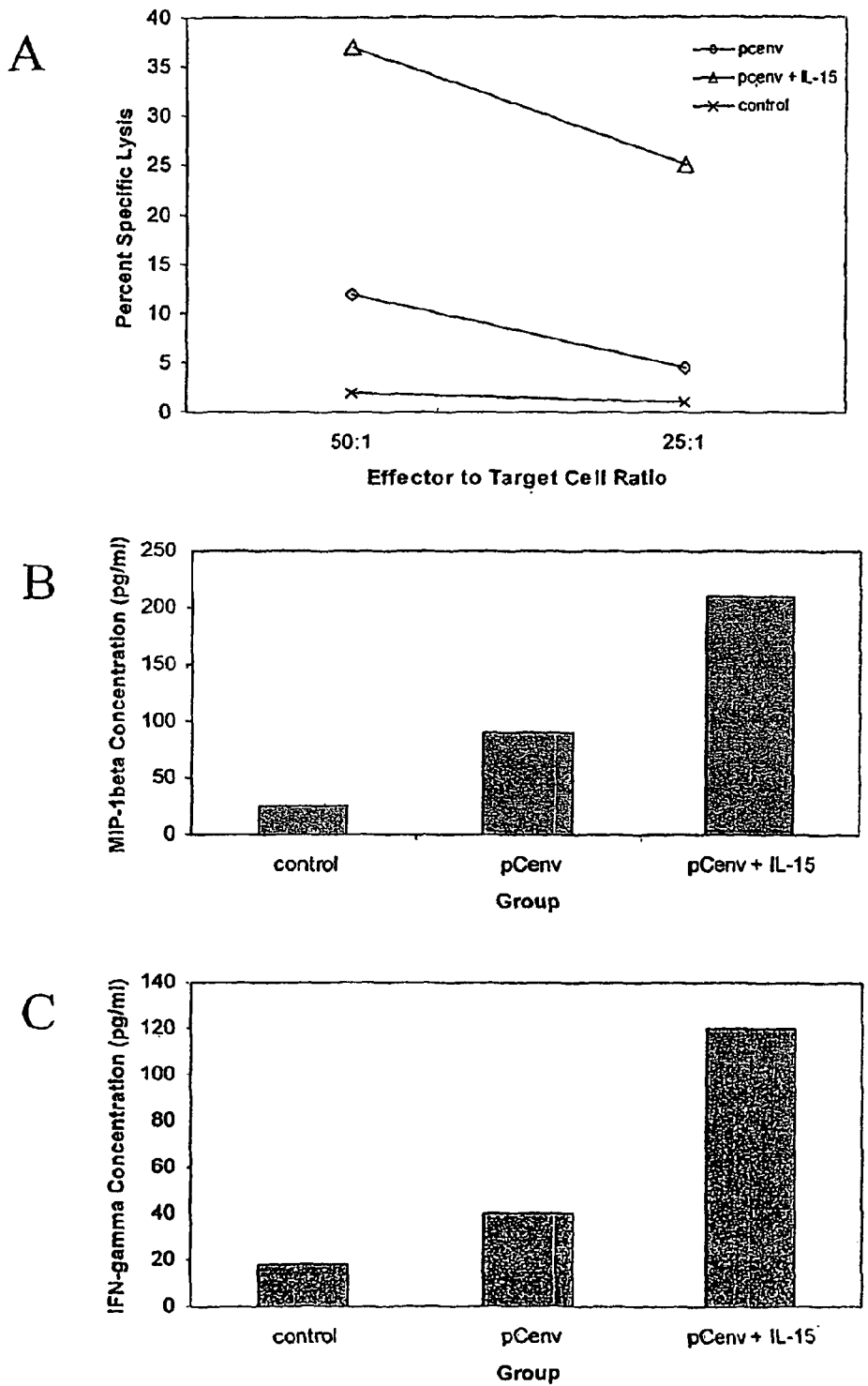
FIG. 4, panels A, B and C depict data from Example 1 showing. HIV-1 antigen specific cellular immune responses following immunization with HIV-1 DNA vaccine and IL-15. Balb/c mice were co-injected at weeks 0 and 2 with 50 μg of pCenv or pCgag with 50 μg of the pIL-15 an IL-15 expressing plasmid. Spleenocytes were harvested two weeks post the final immunization.

The above studies of HIV-1 responses and IL-15 established that IL-15 could enhance IFN-gamma production in primed T cell populations. However, it was unclear what effect IL-15 would have on the functional induction of CD8+ T cells in vivo. To address this question a mouse model system was used. Mice were vaccinated with HIV-1 plasmids as a means of delivering HIV-1 antigens and studying induction of CD8 immunity in vivo. The HIV-1 expressing plasmids were co-injected with either a plasmid that expressed IL-15, or a control plasmid and compared the resulting immune responses. In bulk CTL assays, co-injection with plasmids expressing HIV-1 envelope and LL-15 resulted in nearly 40% lysis of HIV-1 envelope-expressing targets at a 50:1 effector:target ratio compared to 11% lysis observed with envelope plasmid and control vector (FIG. 4, panel A). These results were CD8 T cell dependent and indicate a significant effect of IL-15 on the effector T cell response.

IL-15 Induces MIP-1β and IFN-g Secretion Following Antigen Stimulation in Mice

The vaccine-induced cellular immune responses were further extended by examining the expression profiles of the β-chemokine MIP-1β as a marker of immune activation. Chemokines are important modulators of immune and inflammatory responses. They are especially important in the molecular regulation of trafficking of leukocytes from the vessels to the peripheral sites of host defense. Moreover, it has been previously reported that T cell-produced chemokines including MIP-1β play a critical role in cellular immune expansion (Reference 24 below). Therefore, the level of chemokines produced by stimulated T cells may provide additional insight on the level and the quality of antigen-specific cellular immune response. Supernatant from the stimulated T cells (as described in Materials and Methods) was analyzed and tested for the release of MIP-1β. Co-immunization with IL-15 resulted in high levels of secretion of MIP-1β, (FIG. 4, panel B).

Supernatants were assessed also for production of the Th1 cytokine, IFN-γ. Samples were obtained just prior to the cells being used in the CTL assay following a 3-day lymphocyte stimulation with stimulator cells infected with recombinant vaccinia expressing HIV-1 envelope. FIG. 4, panel C notes that splenocytes from mice co-injected with IL-15 induced higher levels of IFN-γ (120 pg/ml) compared to those injected with the plasmid vaccine alone or control. In contrast, no significant IL-4 production by any culture was observed in these studies (data not shown).

Intracellular Staining for IFN-γ and TNF-α.

Figure 5:
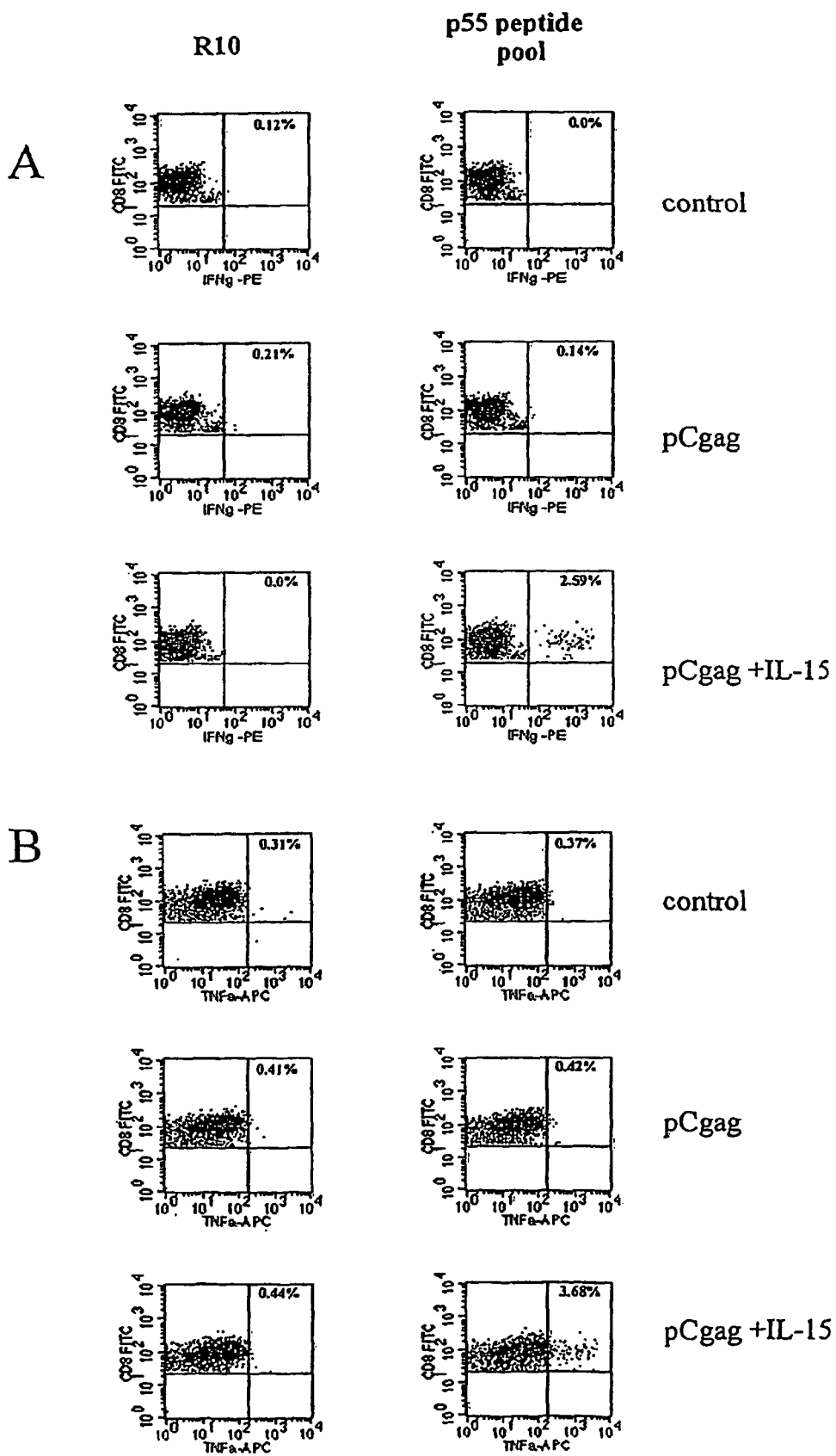
FIG. 5, panels A and B depict data from Example 1 showing intracellular staining for Th1 cytokines. Mice were given two injections with either pCgag alone or pCgag plus pIL-15 DNA plasmids. One week later, splenocytes were harvested and cultured in vitro for five hours in media containing a p55 peptide pool (containing 127 15mers spanning HIV-1 p55 with 11aa overlaps) and Brefeldin A. After stimulation, cells were stained extracellularly with anti-mouse CD3 and anti-mouse CD8 antibodies and then intracellularly with anti-mouse.

To quantitate the T cell response to the HIV-1 vaccines, intracellular cytokine staining assays were performed. Immunized animals were sacrificed and spleenocytes were harvested and cultured in vitro for five hours in media containing the p55 cocktail mix and Brefeldin A. The CD8+ CD3+ T cells were assayed by flow cytometry for production of IFN-γ or TNF-α (FIG. 5, panel A and FIG. 5, panel B). The IL-15 co-vaccinated animals exhibited high CD8 effector T cells responses with 2.6% of CD8+ T cells producing IFN-γ and 3.7% producing TNF-α. These data illustrate that IL-15 exhibited a profound effect on the functional CD8+ T cell response.

Lymphocyte Proliferation of Murine Splenocytes Co-Immunized with IL-15 and HIV-1 Vaccines.

Figure 6:
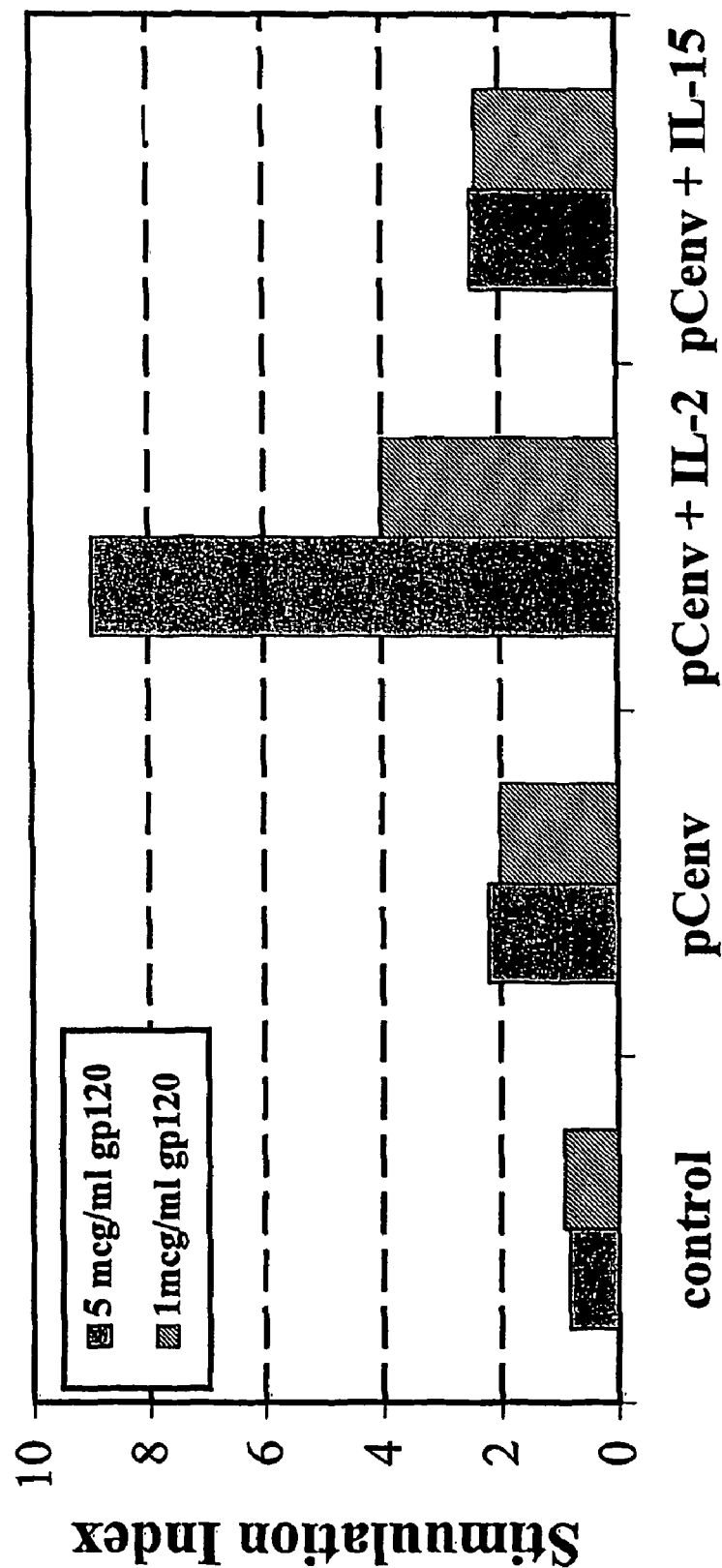
FIG. 6 depict data from Example 1 from murine T helper cell proliferation assays. Balb/c mice were co-injected at weeks 0 and 2 with 50 μg of pCgag or pCenv and 50 μg of the plasmids that express cDNAs of IL-2R-dependent Th1 cytokines IL-2 or IL-15. A 100 μg 1 aliquot containing $5 \times 10^5$ cells was immediately added to each well of a 96 well microtiter flat bottom plate. Recombinant p24 protein was added to wells in triplicate resulting in the final concentration of 5 μg g/ml and 1 μg g/ml. Stimulation Index was determined. Spontaneous count wells included 10% fetal calf serum, which serve as irrelevant protein control. Similarly, pCgag or control routinely have SI of 1 against their irrelevant gp 120 protein. To assure that cells are healthy, PHA or Con A (Sigma) was used as a polyclonal stimulator positive control.

The activation and proliferation of T helper lymphocytes is vital to humoral and cellular immune expansion. Spleenocytes from immunized mice were assessed in a basic lymphocyte proliferation assay for the ability to proliferate in response to stimulation with recombinant HIV-1 antigen. IL-15 did not appear to have a dramatic impact on proliferative responses (FIG. 6). However, IL-2 was used as a control and significant increases in splenocyte proliferation to gp120 env protein in the mice co-injected with IL-2 plasmids were clearly observed. The splenocytes of the mice co-injected with IL-2 resulted in stimulation indexes that were at least 3-fold higher than those of mice immunized with control, pCgag alone, or pCEnv+IL-15 (FIG. 6). This data further illustrates that IL-15 appears to enhance CD8 T cell function without dramatic expansion of T cell help. This also illustrates that this expansion by IL-15 is not dependent on IL-2. This suggests, in such a case, expansion of CD4 as well as CD8 effector function.

Epitope Mapping

Figure 7:
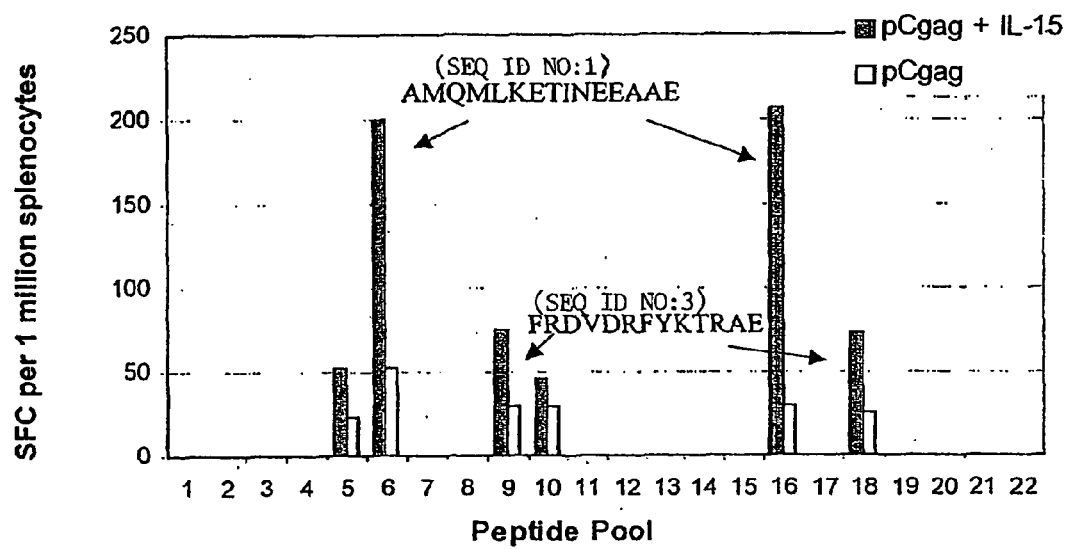
FIG. 7 depict data from Example 1 from epitope mapping of Gag in Balb/c mice following immunization with DNA vaccine pCgag. Balb/c mice were co-injected at weeks 0 and 2 with 50 μg of pCgag and 50 μg of the pIL-15 plasmid or with vector backbone that express genes IL-15 or vector backbone. Spleenocytes were isolated and set-up in a standard ELISPOT assay using a series of peptides. Peptides were mixed in a series of 22 pools in a matrix format and tested for their ability to activate cells to produce IFN-γ.

To resolve the question of whether the enhancement of CD8+ T cell responses with IL-15 treatment was due to an increase in the number of epitopes responded to (i.e. epitope spreading) or due to an overall increase in the number of CD8+ T cells specific for the same epitope. the ELISPOT assay and the series of peptides obtained from the AIDS Reference and Reagent Repository (mixed as pools in a matrix format) was utilized. Two epitopes were identified. The dominant epitope was mapped to Gag amino acids 197 to 211 (AMQMLKETMEEAAE—SEQ ID NO:1) (FIG. 7). Paterson et al have previously defined AMQMLKETI—SEQ ID NO:2 (Reference 35 below) as the dominant CD8 epitope following immunization with a recombinant L. monocytogenes HIV-1 vaccine. A subdominant epitope, Gag amino acids 293-307 (FRDVDRFYKTRAE—SEQ ID NO:3) (FIG. 7) was further defined. There was no increase in the number of epitopes responded to as responses to both epitopes were observed in Gag only immunized groups. However, IL-15 dramatically expanded the magnitude of the responses to these epitopes. Only in the IL-15 co-vaccinated animals was the subdominant epitope clearly evident. IL-15 impacts the expansion of effector CD8 cells.

CD4 Knockout Mice

We observed that IL-15 allowed antigen specific CD8 T cell expansion in PBMCs from HIV-1 infected individuals. We also observed significant CD8 effector cell induction without dependence on CD4 expansion in our vaccine model. Therefore, the contribution of CD4 helper T cells to the IL-15 immune expansion was brought into question. To address this issue, the ability of IL-15 to induce a CD8 effector population in the complete absence of CD4 cells was investigated. Mice homozygous for the $Cd4^{tm1Knw}$ targeted mutation (Reference 36 below) were immunized. These mice have a block in CD4+ T-cell development and therefore most of the circulating lymphocytes are CD8 cells. Utilizing the plasmid co-immunization model where, on average, approximately 200 IFN-gamma producing cells per 1 million spleenocytes in normal mice are induced, in the absolute absence of CD4 cells IL-15 was not able to rescue an induced CD8 effector function (FIG. 8 panel B). As the effect of IL-15 appeared not to be involved in CD4 expansion (FIG. 6) the defect was reasoned to be due to lack of another function provided by T helper cells, CD4 T helper cells also provide help for CD8 expansion through activation of antigen presenting cells (APCs). In this model of APC activation, ligation of CD40, on the APC, to the T cell CD40 ligand upregulates B7 expression which allows for T cell activation. The B7 molecules provide costimulation. for CD8 T cell expansion in the context of MHC class I peptide presentation. Also, Bourgeois et al, (Reference 37 below) demonstrated that CD40L can directly impact CD8 memory cell development.

That the defect in CD4 help was manifesting itself at the level of a lack of costimulation was next considered and explored. To test this hypothesis mice were co-immunized with plasmids containing both IL-15 and CD40L, along with pCgag. An anchored CD40L molecule was used. The anchored CD40L would be expressed locally and in trafficking immune cells but would not be secreted which would complicate the experiment (Reference 38 below). Such vaccination can provide costimulation in trans in a plasmid model (Reference 38 below). Indeed, when pCgag was studied in combination with pCD40L, a Gag specific CD8 immune response was induced in the CD40 KO mice (FIG. 8). This data further indicates that IL-15 impacts directly on memory CD8 lymphocytes. In the absence of CD4 cells IL-15 is not able to induce an antigen specific CD8 cellular response from naïve cells Discussion The maintenance and enhancement an HIV-1 specific CD8 immune response has been the source of much investigation. Recent studies have reported that IL-15 may play an important role in supporting memory cell survival. It was observed in a mouse model that the presence of IL-15 can lead to memory cell division (Reference 39 below). Ex vivo functional analysis as well as studies using transgenic mice genetically lacking IL12, IL-15 or their specific receptors have been important in the characterization of the role played by IL-15. Indeed, Zhang and coworkers (Reference 39 below) demonstrated in an in vivo mouse model that IL-15 provides effective and discriminating stimulation of the memory phenotype, CD44hi CD8+ T cells. And, Ku et al. (Reference 40 below) reported that the division of memory CD8+ T cells is stimulated by IL-15 but is inhibited by IL-2. It was also found that IL-2 inhibited proliferation of CD8+ memory T cells.

The work disclosed herein demonstrates that IL-15 is also particularly effective at inducing CD8+ effector T cells in vitro and in vivo. CD8+ T cells isolated from HIV-1 infected patients were able to secrete IFN-gamma in an antigen specific manner when incubated with peptide and IL-15. IL-15 works in concert with the TCR to stimulate lymphocytes to produce IFN-γ and assume an effector phenotype. In some subjects IL-15 led to production of IFN-γ in the absence of antigen. This suggests that in HIV infection some cells are partially activated and this partial activation state can be rescued by IL-15. However, of importance is that a significant increase in effector function in all subjects when PBMCs were stimulated with both IL-15 and HIV-1 antigens.

Recently, von Adrian and colleagues (Reference 41 below) suggested that IL-15 stimulation of lymphocytes can result in CD8+ T cells proceeding to the memory cell phenotype directly from naïve cells. However, the data herein suggests that engagement of the TCR may lead to more complete activation of CD8+ T lymphocytes indicating that the impact of IL-15 alone on naïve cells would be minimal. In addition, it was suggested that IL-15 leads to memory cells that were non-functional (Reference 41 below). The data herein demonstrates that the IL-15 expansion resulted in fully functional CD8+ T cells as assessed in both the humans as well as the mouse studies. In the mouse, IL-15 dramatically increased CD8+ T cell responses as well as the enhancement of β-chemokine and IFN-γ responses, clearly indicating antigen specific expansion and building on prior work (References 33 and 42 below). This expansion of CD8+ T cell function was observed in the absence of CD4+ T cell expansion. Yet there is an important role for CD4 T cells in the development of the CD8 response. In studies in CD4 knock out mice the need for CD4 T cells could be circumvented by utilizating CD40L. This finding may be critically important for immunotherapy of viral infections.

Many immunotherapy strategies have focused on expanding CD8+ T cell responses. HIV-1 infection complicates immune therapy through viral induced immune suppression that contributes to a lack of effective CD4+ T cell help. In turn, this lack of help is thought to be responsible for an unproductive CD8+ T cell response. In general chronic infections require CD4+ help to maintain control of viral replication and this is likely the case for HIV-1 infection. Serbina et al (Reference 43 below) demonstrated that development of CD8+ cytotoxic T cells are dependent on CD4+ T cells. They further observed that in CD4 T cell knockout mice had decreased IL-15 production. Yet, IL-15 is not produced by CD4+ T cells. It is produced predominantly by stromal cells, monocytes, and macrophages. It is possible that there is some feed back mechanism where CD4+ T cells enhance the production of IL-15, and in the case of decreased CD4 help, ultimately CD8+ T cell functions are decreased. This feed back mechanism may explain why in three of six subjects' production of IFN-γ following the addition of IL-15 alone. In the absence of CD4, and thus at lower levels of IL-15, residual virus may only partially activate CD8+ T lymphocytes in subjects seropositive for HIV-1. Importantly, it appears here that IL-15 can be added in trans to replace defects caused by viral immunosuppression. Implications from this hypothesis should be considered in the area of immune therapy for HIV-1.

In summary IL-15 expanded CD8+ T cell effector function in mice and expanded functionality of CD8+ T cells isolated from subjects positive for HIV-1 infection. The use of IL-15 as a supplement to active immune therapy should be considered as an adjunct therapy to HAART.

REFERENCES

Which are Each Incorporated Herein by Reference

1. Ho, D., 1996, Therapy of HIV infections: problems and prospects. Bull. New York Acad. Med. 73, 37-45.
2. Finzi, D., Hermankova, M., Pierson, T., Carruth, L M., Buck C., 1997, Identification of a Reservoir for HIV-1 Patients on Highly Active Antiviral Therapy, Science, 278: 1295-1300.
3. Wong, J., Hezareh, M., Gunthard, H., Havlir, D V., 1997, Recovery of Replication-Competent HIV Despite Prolonged Suppression of Plasma Viremia, Science, 278: 1291-1294.
4. Rosenberg, E S., Altfeld, M., Poon, S H., Phillips, M N., Wilkes, B M., Eldridge, R L., Robbins, G K., D Aquilia R, T. Goulder, P J R, Walker, B D, 2000, Immune control of HIV-1 after early treatment of acute infection, *Nature,* 407: 523.
5. Koup R, Safrit J, Cao Y, 1994, Temporal association of cellular immune responses with the initial control of viremia in primary Human immunodeficiency virus type 1 syndrome. *J of Virol,* 68:4650-4655.

6. Rinaldo C, Huang X, Fan Z, 1995, High Levels of Anti-Human Immunodeficiency Virus Type 1 (HIV-1) Memory Cytotoxic T-Lymphocyte Activity and Low Viral Load Are Associated with Lack of Disease in HIV-1 Infected Long-Term Nonprogressors, *J Virol.*, 69:5838-5842.

7. Cao, H., Kanki, P., Sankale, J., 1997, Cytotoxic T Lymphocyte Cross-Reactivity among Different HIV-1 Type 1 Clades: Implication for Vaccine Development, *J Virol;* 71:86158623.

8. Rowland-Jones S, Nixon D, Aldhous M., 1993, HIV-specific cytotoxic T-cell activity in an HIV-exposed but uninfected infant. *Lancet,* 341:860-86.

9. Rowland-Jones S, Sutton J, Ariyoshi K, 1995. HIV-specific T-cells in HIV-exposed but uninfected Gambian women. *Nature Medicine,* 1:59-64

10. Borrow, P, Lewicki, H, Wei, S, 1997, Antiviral pressure exerted by HIV-1 specific cytotoxic T lymphocytes during primary infection demonstrated by rapid selection of CTL escape virus *Nature Medicine,* 3:205-211.

11. Borrow, R. Shaw G M, 1998, Cytotoxic lymphocyte escape viral variant how important are they in viral evasions of immune clearance in vivo, Immunology Rev, 164: 37-51.

12. Goulder P J, Phillips R E, Colbert R A 1997, Late escape from an immunodominant cytotoxic T lymphocyte response associated with progression to AIDS, *Nature Medicine,* 3; 212-217.

13. Goulder P J, Sewell A K, Lalloo D G, 1997, Pattern of immunodominance in HIV-1 specific cytotoxic T lymphocyte response in two human histocompatibility leukocyte antigens HLA identical siblings with HLA A0201 are influence by epitope mutations. *J Exp Med,* 185:1423-1433.

14. Phillips R E, Rowland-Jones, S Nixon, D F, 1991, Human immunodeficiency virus genetic variation that can escape cytotoxic T cell recognition Nature, 354; 453-459.

15. Koup, R A, 1994, Virus Escape from CTL recognition, *J Exp Med,* 180; 779-782.

16. Ayyavoo, V., Mahboubi, A., Mahalingam, S., Ramalingam R., Kudchodkar, S., Williams, W V., Green, D R., Weiner, D B, 1997, HIV-1 vpr suppresses immune activation and apoptosis through regulation of nuclear factor KB, *Nature Medicine,* 3:1117-1122.

17. Kerkau, T., Bacik I., Bennink, J R., Yewdell, J W., Huning, T., Schimpll, A., Schubert, U, 1997, The human immunodeficiency virus type I (HIV-1) vpu protein interferes with an early step in the biosynthesis of major histocompatibility complex (MHC) class I molecules, *J Exp Med.,* 185: 1295-1305.

18. Lenburg, M. E., and Landau N. R., 1993, VPU induced degradation of CD4: Requirement for specific amino acid residues in the cyotplasmic domain of CD4, *J Virol,* 67:6542-6550.

19. Anderson, S., Shugar, D. C., SwanstrOM, R., Garcia, J. V., 1993, Nef from primary isolates of human immunodeficiency virus type I suppressed surface CD4 expression in human and mouse T cells *J Virol* 67:4923-4931.

20. Rosenberg, E S, Billings, J M, Caliendo, A M, et al., Vigorous HIV-1 Specific CD4 T cell Responses Associated with Control of Viremia, Science, 278:1447-1450, (1997).

21. Kalam, S A, Walker B D., 2000, The critical need for CD4 help in maintaining effective cytotoxic T Shankar P. Russo M. Harnisch B. Patterson M. Skolnik P. Lieberman J. Impaired function of circulating HIV-specific CD8(+) T cells in chronic human immunodeficiency virus infection. *Blood.* 96(9):3 094-101

22. Murali-Krishna, K., Lau., L L., Sambliara, S., Lemonnier, F., Altman, J., Ahmed, R., 1999, Persistence of Memory CD8 T Cells in MHC Class I-Deficient Mice, *Science,* 286:1377-1383.

23. Tagaya, Y., Bamford, R N., Defilippis, A P, Waldmann, T A., 1996, IL-15: A Plenotropic Cytokine with Diverse Receptor/Signaling Pathways Whose Expression is Controlled at Multiple Pathways. *Immunity* 4:329-336.

24. Chang, K H, Kim, J M, Kim H Y, Sorig, Y G, Choi, Y H, Park, Y S, Cho, J H, Hong, S K., 2000, Spontaneous Programmed Cell Death of Peripheral Blood Mononuclear Cells from HIV-Infected Persons is Decreased with IL-15. *Yonsei Medical Journal,* 41:112-118.

25. Naora H., Gougeon, M L., 1999, Enhanced Survival and Potent Expansion of the Natural Killer Population of HIV Infected Individuals by Exogenous IL-15. *Immunology Letters,* 68:359-367.

26. Lin, S J, Roberts, R L, Ark, B J, Nguyen, O H, Thomas, E H, Stichn, E R., 1997, Human Immunodeficiency Virus (HIV) Type-1 GP120-Specific Cell Mediated Cytotoxicity Interleukin-2 (IL-2), IL-12, and IL-15. *Clin. Imm. Immpath,* 82:163-173.

27. Loubeau, M., Ahmad A., Toma E., Menezes, J., 1997, Jo. Enhancement of Natural Killer and Antibody Dependent Cytotoxic Activities of the Peripheral Mononuclear Cells of HIV-Infected Patients by Recombinant IL-15. *AIDS* 16:137-145.

28. Kacani, L., Sprizl G M., Erdei, A., Dierich, M P, 1999, Interleukin-15 Enhances HIV-1 Driven Polyclonal B-Cell Response in Vitro. *Exp and Clin Immun,* 16:167-179.

29. Kacani, L., Stoiber H., Dierich, M P, 1997, Role of IL-15 in HIV-1 Associated Hypergammaglobulinanemia. *Clin Exp Imm* 108:14-18.

30. Agostini, C., Zambello, R., Perrin A., Piazzo, F., Siviero, M., Basso, U., Borfolin, M., Trentin L., Semenatao, G., 1999, CD8 T-Cell Infiltration in Extravascular Tissues of Patients with Human Imunodeeiciency Virus Infection. Interleukin 15 Upmodulates Co-Stimulatory Pathways Involved in the Antigen Presenting Cells of T-cell Interaction. *Blood,* 93:1277-1286.

31. Patki, A H., Quinone S., Mateo, M E., Dorazio, D., Yen-Lieberman B., Boom W H, Thomas, E K., Ledermann M M, 1996, Activation of antigen Inducaed Lymphocyte Proliferation by Interleukin-15 Without the Mitogenic Effect og Interleukin-2 That May Induce Human Immunodefeciency Virus-1 Expression. *JCI,* 98:616-621.

32. Lucey D R., Pinto L A, Bethke, F R., Rusnak J., Mekher G P, Hashemi, F N, Landay, A L., Kessler, H A, Paxton, R J., Grabstein, K., Shearer G M., In Vitro Immunologic and Virologic Effects of Interleukin-15 on Peripheral Blood Mononuclear Cells from Normal Donors and Human Immunodeficiency Virus Type-1 Infected Patients. *Clin Diagn Lab Imm,* 4:43-48.

33. Kim, J J. Trivedi, N N., Nottingham, L K., Morrison, L., Tsai, A., Hu, Y., Mahalingarn, S., Dang, K., Alm, L., Doyle, N K., Wilson, D., Chattergoon, M A., Chalian, A A., Boyer, J D., Agadjanyan, M., Weiner, D B., 1998, Modulation of amplitude and direction of in vivo immune responses by co-administration of cassettes with DNA immunogens, *Eur. J Immunol.* 28:1089-1103.

34. Kim J J. Tsai A. Nottingham L K. Morrison L. Cunning D M. Oh J. Lee D J. Dang K. Dentchev T. Chalian A A. Agadjanyan M G. Weiner D B, 1999, Intracellular adhesion molecule-1 modulates beta-chemokines and directly costimulates T cells in vivo, *Journal of Clinical Investigation.* 103:869-77.

35. Mata, M., Travers, P J. Liu, Q., Frankel, F R., Paterson, Y., 1998, The MHC Class I Restricted Immune Response to HIV-1 gag in Balb/c Mice Selects a Single Epitope That Does not Have a Predictable MHC Binding-Motif and Binds to Kd Through Interactions Between a Glutamine at PS and Pocket D, Jo of Immun., 161:2985-2993.

36. McCarrick III J W, Parties J R, Seong R H, Solter D, Knowles B B. 1993. Positive-negative selection gene targeting with the diphtheria toxin A-chain gene in mouse embryonic stem cells. Transgenic Res 2:183-190.

37. Bourgeois, C., Rocha, B., Tanchot, C., A Role for CD40 Expression on CD8+ T Cells in the Generation of CD8+ T Cell Memory, 2002, Science 297:2060-2063.

38. Sin J I. Kim J J. Zhang D. Weiner D B. Modulation of cellular responses by plasmid CD40L: CD40L plasmid vectors enhance antigen-specific helper T cell type 1 CD4+ T cell-mediated protective immunity against herpes simplex virus type 2 in vivo. *Human Gene Therapy.* 12:1091-102, 2001.

39. Zhang, X., Sun, S., Hwang, I., Tough, D F. Sprent, 1998, J., Immunity, 8:591-599.

40. Ku, C C., Murakami, M., Sakamoto, A., Kappler, J., Marrack. P., 2000, Control of Homerostasis of CD8 Memory T Cells by Opposing Cytokines, Science, 288: 675-678.

41. Manjunath, N., Shankar, P., Wan, J., Weninger, W., Crowley, M A. Hieshmina, K., Springer, T A., Fan, X., Shen, H., Lieberman, J., von Andrian, U H., 2001, Effector differentiation is not prerequisite for generation of memory cytotoxic T lymphocytes, *Journal of Clinical Investigation,* 108:871-878.

42. Moore A C. Kong W P. Chakirabarti B K. Nabel G J. Effects of antigen and genetic adjuvants on immune responses to human immunodeficiency virus DNA vaccines in mice. *Journal of Virology.* 76(1):243-50, 2002 January 43. Serbina N V. Lazarevic V. Flynn J L 2001, CD4(+) T cells are required for the development of cytotoxic CD8(+) T cells during *Mycobacterium tuberculosis* infection. Journal of Immunology. 167:6991-7000.

Example 2

Figure 9:
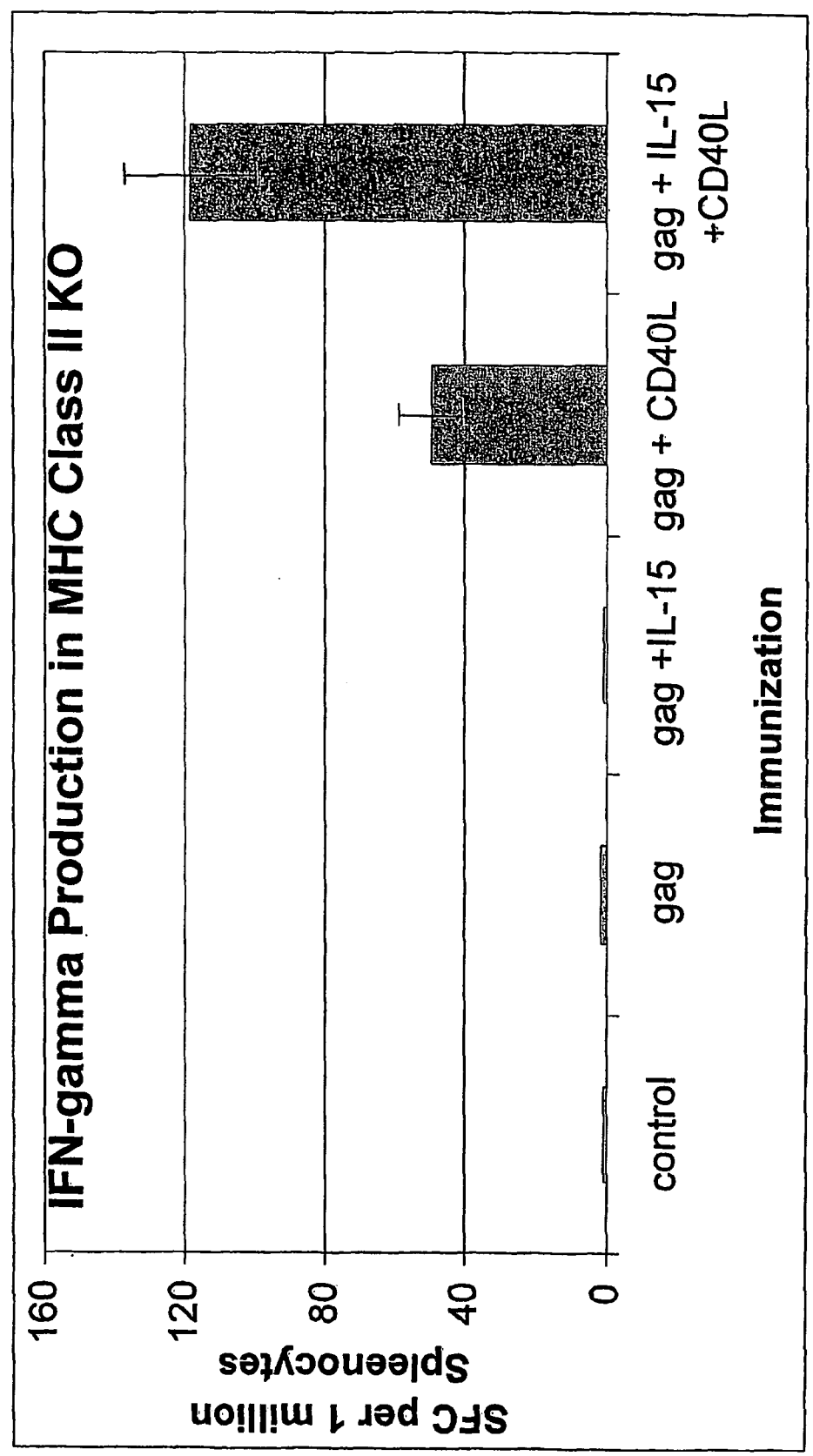
FIG. 9 depict data from Example 2 showing local production of IL-15 and CD40L at the vaccine site can replace the requirement for T cell help for expansion of CD8 effector T cells.

There is a requirement for CD4(+) Th cells and the production of IFN-gamma to control viral replication in immune compromised individuals as well as in antitumor immunology. Data from experiments performed demonstrate that the requirement for T cell help for expansion of CD8 effect or T cells can be replaced by local production of IL-15 and CD40L at the vaccine site. Experiments using mice in which CD4(+) T cells were eliminated by gene knockout of the MHC class II beta-chain (MHC II KO), reveal that priming of the animals with antigen gag+IL-15+CD40L leads to activation of CD8 T cells. Activation is measured by IFN-gamma production as spots. Greater than 50 spots in this assay are positive. These data, shown in FIG. 9, illustrate a simple method for the activation of effect or CD8 T cells independently of CD4(+) T cell help. These studies have importance for the treatment of immunocompromised individuals.

Example 3

Human, mouse, and simian IL-15 cDNA encodes a 162 amino acid (aa) residue precursor protein containing a 48 aa residue leader that is cleaved to generate the 114 aa residue mature IL-15. Human IL-15 shares approximately 97% and 73% sequence identity with simian and mouse IL-15, respectively. Both human and simian IL-15 are active on mouse cells. Although the structure of IL-15 has not been determined, it is predicted to be similar to IL-2 and other members of the four-helix bundle cytokine family. (Grabstein, K. et al. (1994) Science 264:965, Anderson, D. M. et al. (1995) Genomics 25:701; and Bamford, R. N. et al. (1995) Cytokine 7:595, Brandhuber, B. J. et al. (1987) Science 238:1707, both of which are incorporated herein by reference.)

IL-15 mRNAs have been detected in heart, lung, liver, placenta, skeletal muscle, adherent peripheral blood mononuclear cells, APCs (Dendritic cells), and epithelial and fibroblast cell lines. However, IL-15 mRNA is not detectable in activated peripheral blood T cells that contain high levels of IL-2 mRNA. IL-15 has been shown to stimulate the growth of natural killer cells, activated peripheral blood T lymphocytes, tumor infiltrating lymphocytes (TILs), and B cells. In addition, IL-15 has also been shown to be a chemoattractant for human blood T lymphocytes, to induce lymphokine-activated killer (LAK) activity in NK cells, and to induce the generation of cytolytic effector cells. (Armitage, R. J. et al. (1995) J. Immunol. 154:483; P. Wilkinson and F. Liew (1995) J. Exp. Med. 181:1255; Grabstein, K. et al. (1994) Science 264:965; Giri, J. G. et al. (1994) EMBO J. 13:2822; and Giri, J. G. et al. (1995) EMBO J. 15:3654, each of which is incorporated herein by reference.)

Because IL-15 is a prototypic Th1 cytokine, and by virtue of its activity as a stimulator of T cells, NK cells, LAK cells, and TILs, IL-15 is an exciting candidate for use as a molecular adjuvant along with DNA vaccines such as HIV vaccines to enhance cellular immune responses. IL-15 expands HIV specific CTLs, and overproduction of IL-15 is associated with inflammatory diseases such as Crohn's disease.

Northern Blot analysis indicates widespread constitutive expression of IL-15. Control of expression occurs post-transcriptionally at the level of translation and translocation (intracellular trafficking). IL-15 mRNA includes a number of elements that impede its translation into protein including: 1) the 5' AUGs are burdened with upstream AUGs that interfere effective IL-15 translation (5 in mice, 12 in humans); 2) the start codon for the IL-15 coding sequence has a weak KOZAK context (GTAATGA); and 3) presence of a negative element in the C-terminus of the IL-15 mature protein coding sequence. (Grabstein et al., (1994) Science 264:965-968, Bamford et al., (1996) PNAS 93:2897-2902; Bamford et al., (1998) J. Immunol 160:4418-4426; and Kozak et al., (1991) J. Cell Biol. 115:887-903, which are each incorporated herein by reference. Each of these three controls may be eliminated to improve expression.

Native IL-15 isoforms contain two leader peptides: a 21 aa signal peptide (SSP) or a 48 aa signal peptide (LSP) (Waldmann et al. Ann. Rev>Immunol. (1999) 17:19-49, which is incorporated herein by reference.

The following strategy for increasing expression of IL-15 through optimization of IL-15 DNA constructs for immunization was followed. Primers were designed to amplify IL-15 from start of signal peptide, thus upstream inhibitory AUGs are not present in the final IL-15 message. Primers were designed to include a strong KOZAK context (GCCGCCACC). The C-terminus negative regulatory element was removed using PCR antisense primer design. The primers are set forth in FIG. 10.

The following strategy for increasing expression of IL-15 through replacement of the 48 amino acid IL-15 signal peptide (LSP) with IgE leader was performed. Sense primers were designed to start after 48 aa LSP while antisense primer amplified from stop site. Primers were designed to include a strong KOZAK context (GCCGCCACC—SEQ D NO:4).

Sense primer was designed to contain the sequence for IgE leader sequence plus a ATG start site. The primers are set forth in FIG. 11.

Figure 12:
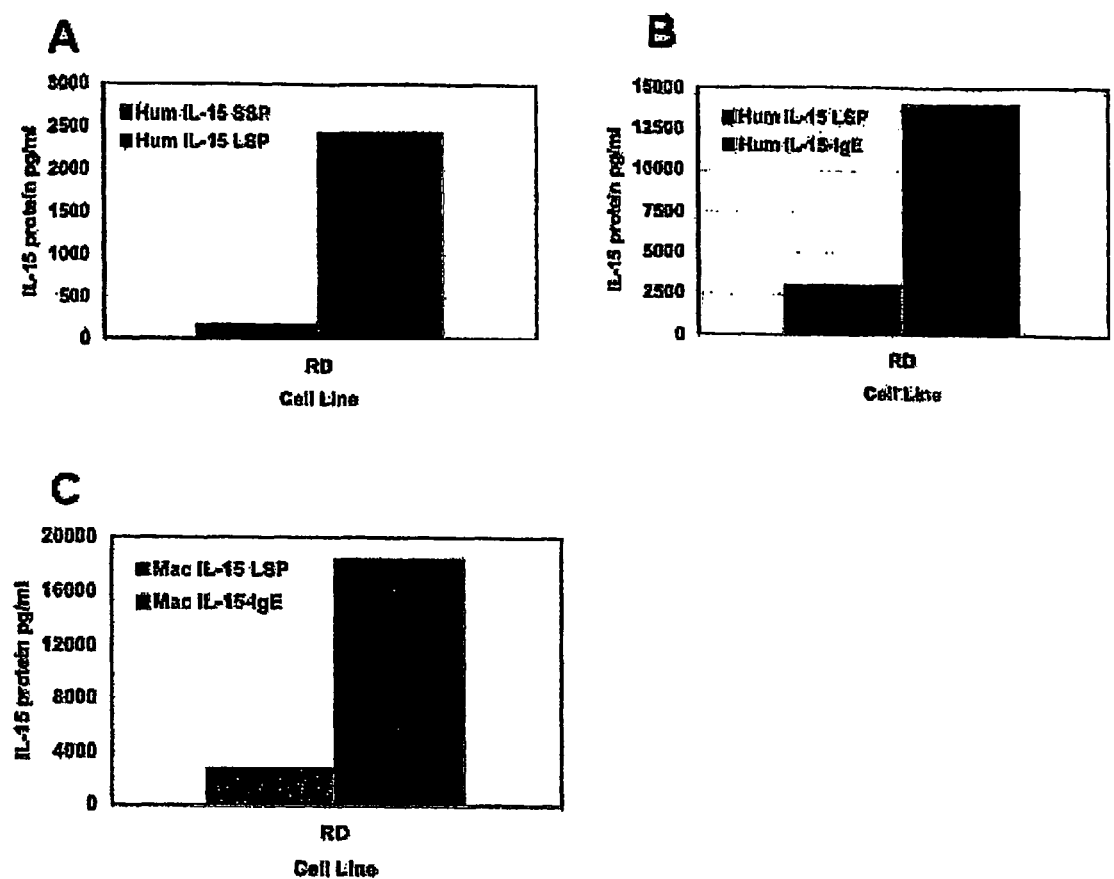

Various constructs were prepared and used to transfect RD cells. IL-15 protein production was measured for the various constructs. The data is shown in FIG. 12, panels A-C. FIG. 13A shows a comparison of expression by human constructs that include coding sequences for the 21 amino acid signal peptide linked to IL-15 (IL-15 SSP—left) and coding sequences for the human 48 amino acid signal peptide (IL-15 LSP—right). FIG. 12, panel B shows a comparison of expression by human constructs that include coding sequences for the 48 amino acid signal peptide (human IL-15 LSP—left) and coding sequences for the IgE signal peptide (human IL-15-IgE—right). FIG. 12, panel C shows a comparison of expression by Macaque constructs that include coding sequences for the 48 amino acid signal peptide (Mac IL-15 LSP—left) and coding sequences for the IgE signal peptide (Mac IL-15-IgE—right).

Figure 13:
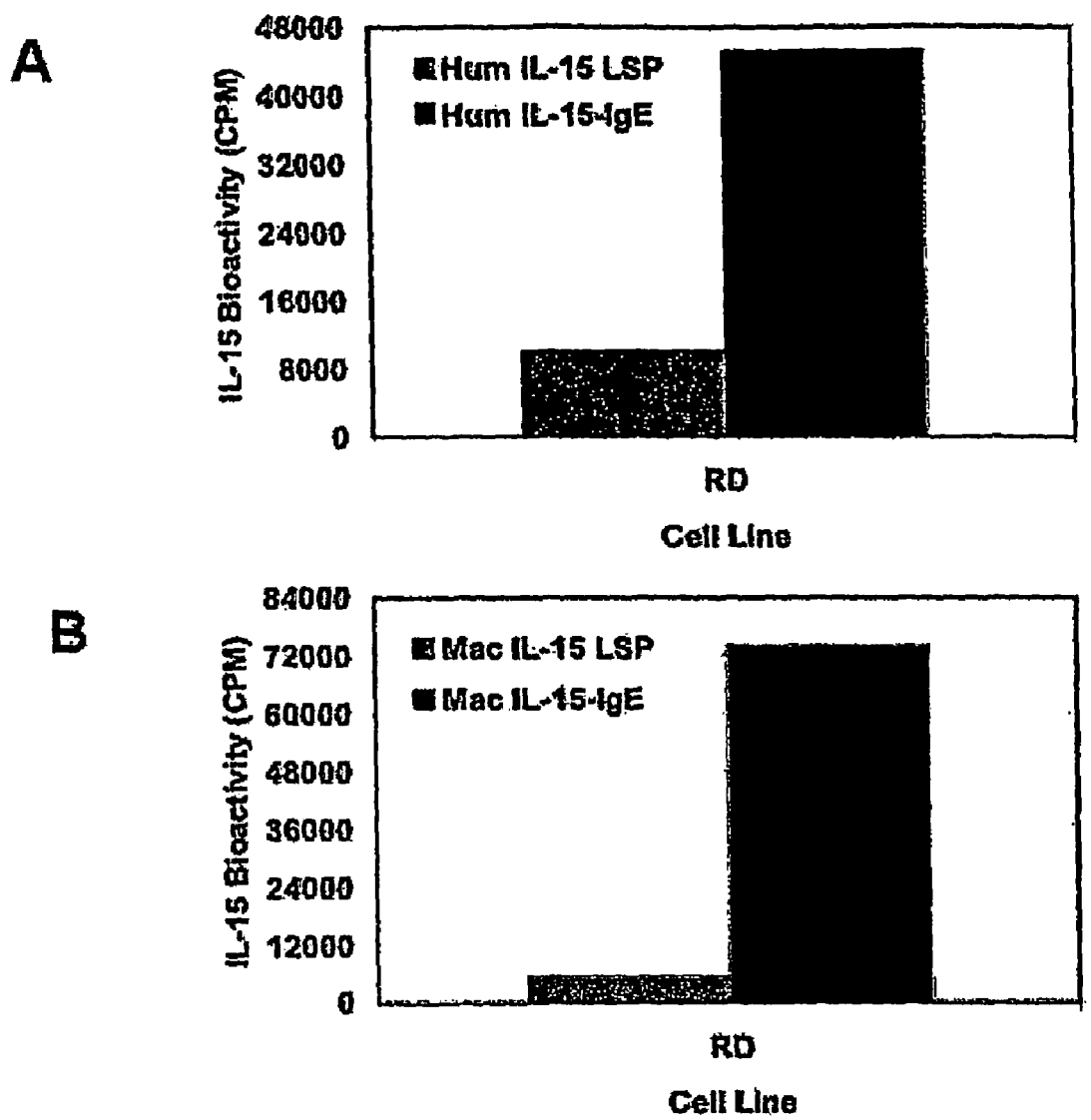

IL-15 bioactivity was measured of IL-15 protein produced from the various constructs. The data is shown in FIG. 13 panels A and B. FIG. 13, panel A shows a comparison of IL-15 bioactivity between human constructs that include the 48 amino acid signal peptide (human IL-15 LSP—left) and coding sequences for the IgE signal peptide (human IL-15-IgE—right). FIG. 13, panel B shows a comparison of IL-15 bioactivity between Macaque constructs that include coding sequences for the 48 amino acid signal peptide (Mac IL-15 LSP—left) and coding sequences for the IgE signal peptide (Mac IL-15-IgE—right).

Figure 14:
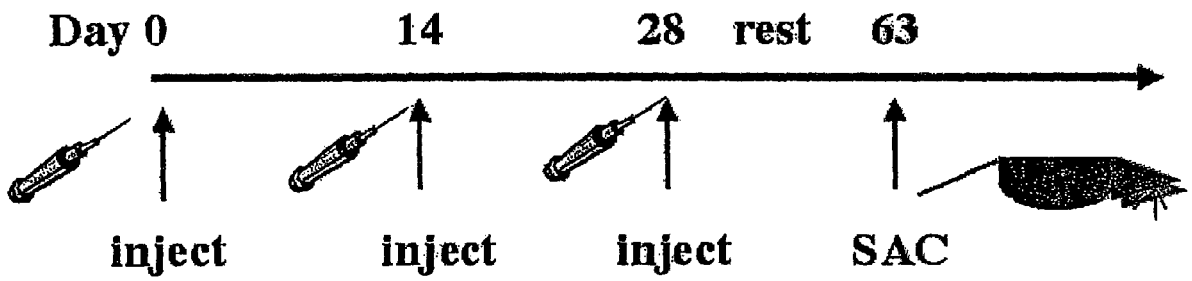

A construct was made using the expression vector pVAX with an insertion of an IL-15 coding sequence linked to coding sequence for an IgE signal peptide. Construct encoding HIV-1 Gag were also generated. Immunological experiments were performed comparing the effects on immune responses using IL-15 engineered plasmids in combination with HIV-1 Gag. Balb/c Mice were vaccinated according to the immunization schedule shown in FIG. 14.

Figure 15:
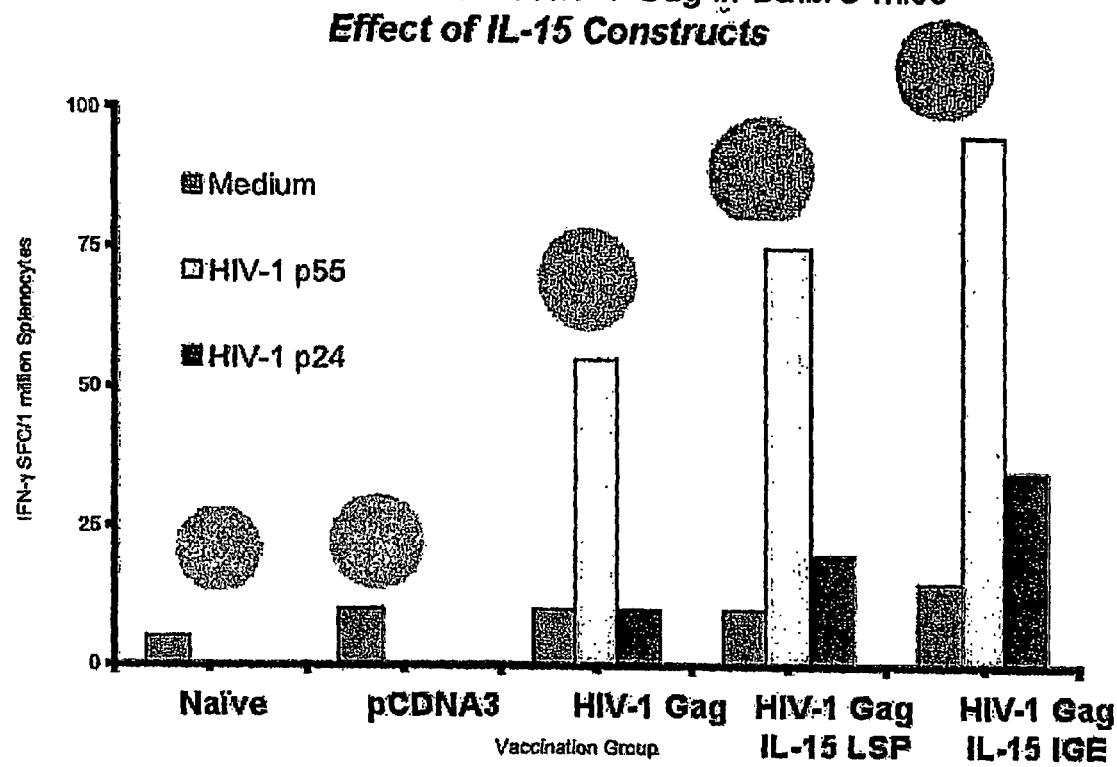

Immune responses were studied by comparing restimulation of antigen-specific IFN-γ production 5 weeks following the third immunization. The data is shown in FIG. 15. Vaccine groups included naïve mice, mice vaccinated with the vector pCDN3, mice vaccinated with constructs that encoded HIV-1 Gag, mice vaccinated with constructs that encoded HIV-1 Gag and IL-15 linked to the 48 amino acid signal peptide and mice vaccinated with constructs that encoded HIV-1 Gag linked to the IgE signal peptide.

Example 4

Figure 16:
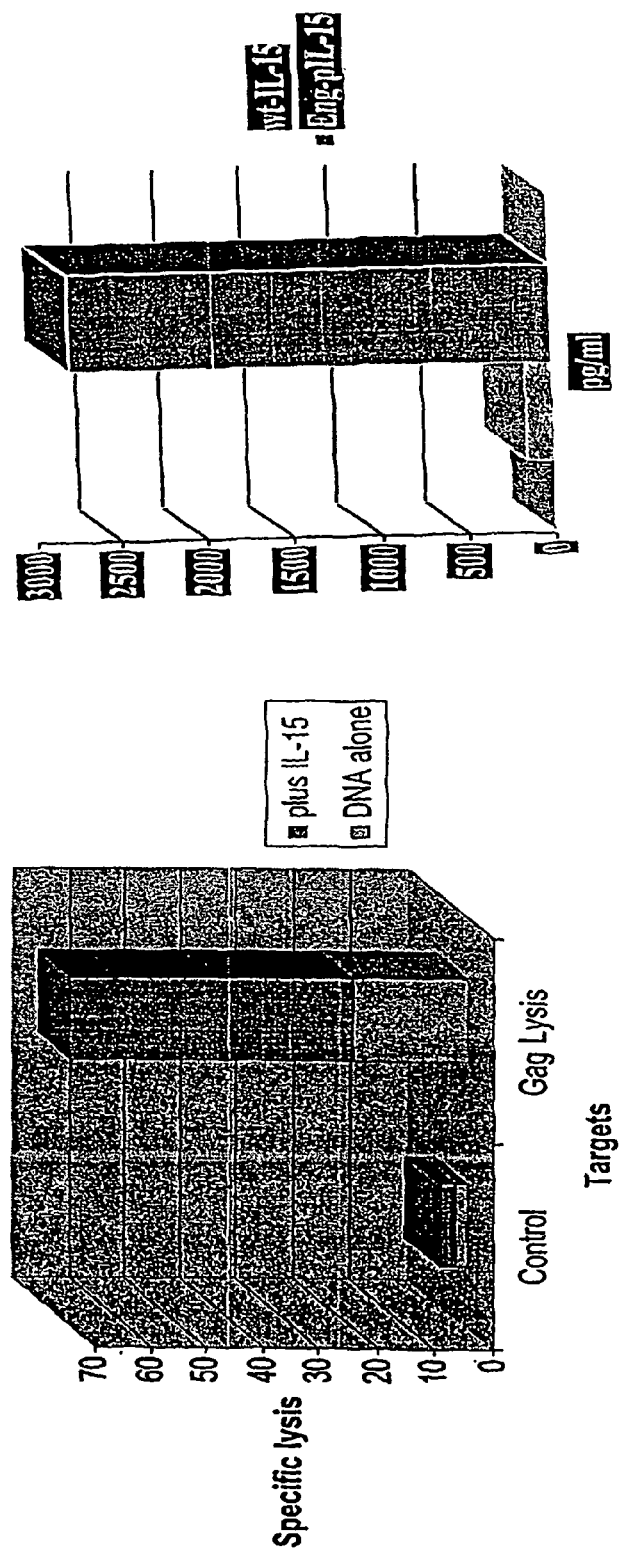
FIG. 16 refers to data from the disclosure set forth in Example 4.

An engineered IL-15 plasmid vaccine was constructed by removing the native IL-15 Kozak region, AUG's and UTRs. The engineered IL-15 plasmid was provided with the coding sequence for IgE signal peptide. The engineered IL-15 was expressed at a level 30 to 50 times greater than that observed with a comparable wild type plasmid. The immune response observed in mice co-immunized with engineered IgE signal-IL-15 and HIV-1 gag constructs were significantly times greater than mice immunized with the HIV-1 gag construct alone. Data is shown in FIG. 16.

Example 5

Isolated cDNA that encodes the immunomodulating proteins are useful as a starting material in the construction of constructs that can produce that immunomodulating protein. In some embodiments, constructs are provided in which coding sequences for one of the following immunomodulatory proteins are linked to the IgE signal peptide. In some embodiments, such constructs are provided as part of vaccines and immunomodulating compositions such as those described herein.

Using standard techniques and readily available starting materials, a nucleic acid molecule that encodes an immunomodulating protein may be prepared and incorporated into constructs, vectors, vaccines etc as described herein.

Genbank Accession number AF031167 refers to the complete coding sequence of human IL-15 mRNA. Genbank Accession numbers Y09908, X91233, X94223 and X94222 also refer to human IL-15 sequences. Each sequence is incorporated herein by reference.

Genbank Accession number L07414 refers to the complete coding sequence of human CD40-ligand mRNA. The sequence is incorporated herein by reference.

The GENBANK Accession number for the nucleotide and amino acid sequences for Bax is L22473, which is incorporated herein by reference.

The GENBANK Accession number for the nucleotide and amino acid sequences for TRAIL is U37518 or AF023849, which are incorporated herein by reference.

The GENBANK Accession number for the nucleotide and amino acid sequences for TRAILrecDRC5 is U90875 or AF016266, which are incorporated herein by reference. Also incorporated by reference are TRAIL-R2 AF016849; TRAIL-R3 AF014794; and TRAIL-R4 AF021232.

The GENBANK Accession number for the nucleotide and amino acid sequences for RANK is AF018253 which is incorporated herein by reference.

The GENBANK Accession number for the nucleotide and amino acid sequences for RANK LIGAND is AF019047 or AF333234, which are incorporated herein by reference.

The GENBANK Accession number for the nucleotide and amino acid sequences for Ox40 is X75962, which is incorporated herein by reference.

The GENBANK Accession number for the nucleotide and amino acid sequences for Ox40 LIGAND is X79929 or AB007839, which are incorporated herein by reference.

The GENBANK Accession number for the nucleotide and amino acid sequences for NKG2D is AF461811 or X54870, which are incorporated herein by reference.

The GENBANK Accession number for the nucleotide and amino acid sequences for MICA is X92841, which is incorporated herein by reference.

The GENBANK Accession number for the nucleotide and amino acid sequences for MICB is U65416, which is incorporated herein by reference.

The GENBANK Accession number for the nucleotide and amino acid sequences for NKG2A is X54867, which is incorporated herein by reference.

The GENBANK Accession number for the nucleotide and amino acid sequences for NKG2B is X54868, which is incorporated herein by reference.

The GENBANK Accession number for the nucleotide and amino acid sequences for NKG2C is X54869 or Aj0016984, which are incorporated herein by reference.

The GENBANK Accession number for the nucleotide and amino acid sequences for NKG2E is L14542, which is incorporated herein by reference.

The GENBANK Accession number for the nucleotide and amino acid sequences for NKG2F is AH006173, U96845 or U96846, which are incorporated herein by reference.

The GENBANK Accession number for the nucleotide and amino acid sequences for CD30 is M83554, (Durkop, H et al. Cell 68 (3), 421-427 (1992)) which is incorporated herein by reference.

The GENBANK Accession number for the nucleotide and amino acid sequences for CD153 (CD30L) is L09753, (Smith, C. A., et al. Cell 73 (7), 1349-1360 (1993)) which are incorporated herein by reference The GENBANK Accession number for the nucleotide sequence for Fos is K00650 or V01512, which are each incorporated herein by reference.

The GENBANK Accession number for the nucleotide sequence for c-jun J04111 or M29039, which are each incorporated herein by reference.

The GENBANK Accession number for the nucleotide sequence for Sp-1 is BC021101, BC005250, BC002878, M31126, J02893 or X15102, which are each incorporated herein by reference.

The nucleotide sequence for Ap1 can be identified as described in Lee et al, 1987 Cell 49:741-752, Rauscher et al. 1988 Science 240:1010-1016, and Chiu et al, 1988 Cell 54:541-552, which are each incorporated herein by reference.

The GENBANK Accession number for the nucleotide sequence for Ap-2 is M36711, which is incorporated herein by reference.

The GENBANK Accession number for the nucleotide sequence for p38 is U66243, which is incorporated herein by reference.

The GENBANK Accession number for the nucleotide sequence for p65Rel is L19067, which is incorporated herein by reference.

The GENBANK Accession number for the nucleotide sequence for MyD88 is U70451, which is incorporated herein by reference.

The GENBANK Accession number for the nucleotide sequence for IRAK is NM001569, which is incorporated herein by reference.

The GENBANK Accession number for the nucleotide sequence for TRAF6 is U78798, which is incorporated herein by reference.

The nucleotide sequence for IkB can be found as described in Gilmore et al. Trends Genet 1993 December; 9(12):427-33, which is incorporated herein by reference.

The GENBANK Accession number for the nucleotide sequence for NIK is Y10256, which is incorporated herein by reference.

The nucleotide sequence for SAP K can be found as described in Franklin et al. Oncogene. 1995 Dec. 7; 11(11):2365-74, which is incorporated herein by reference.

The GENBANK Accession number for the nucleotide sequence for SAP1 is M85164 or M85165, which are each incorporated herein by reference.

The GENBANK Accession number for the nucleotide sequence for JNK2 is L31951, which is incorporated herein by reference.

The GENBANK Accession number for the nucleotide sequence for JNK1B2 is U35005; which is incorporated herein by reference.

The GENBANK Accession number for the nucleotide sequence for JNK1B1 is U35004; which is incorporated herein by reference.

The GENBANK Accession number for the nucleotide sequence for JNK2B2 is U35003; which is incorporated herein by reference.

The GENBANK Accession number for the nucleotide sequence for JNK2B1 is U35002; which is incorporated herein by reference.

The GENBANK Accession number for the nucleotide sequence for JNK1A2 is U34822; which is incorporated herein by reference.

The GENBANK Accession number for the nucleotide sequence for JNK2A1 is U34821; which is incorporated herein by reference.

The GENBANK Accession number for the nucleotide sequence for JNK3A1 is U34820; which is incorporated herein by reference.

The GENBANK Accession number for the nucleotide sequence for JNK3A2 is U34819, which is incorporated herein by reference.

The GENBANK Accession number for the nucleotide sequence for NF-kappa-B2, p49 splice form is A57034, which is incorporated herein by reference.

The GENBANK Accession number for the nucleotide sequence for NF-kappa-B2, p110 splice form is A42024, which is incorporated herein by reference.

The GENBANK Accession number for the nucleotide sequence for NF-kappa-B2, p105 splice form is S17233, which is incorporated herein by reference.

The GENBANK Accession number for the nucleotide sequence for NF-kappa-B 50K chain precursor is A37867, which is incorporated herein by reference.

The nucleotide sequence for NFkB p50 is described in Meyer R., et al. (1991) Proc. Natl. Acad. Sci. USA 88(3), 966 970, which is incorporated herein by reference.

The nucleotide and amino acid sequences of human IL-1α are well known and set forth in Telford, et al. (1986) Nucl. Acids Res. 14:9955-9963, Furutani, et al. (1985) Nucl. Acids Res. 14:3167-3179, March, et al. (1985) Nature 315:641-647, and accession code Swissprot PO1583, which are each incorporated herein by reference.

The nucleotide and amino acid sequences of human IL-2 are well know and set forth in Holbrook, et al. (1984) Proc. Natl. Acad. Sci. USA 81:1634-1638, Fujita, et al. (1983) Proc. Natl. Acad. Sci. USA 80:7437-7441, Fuse, et al. (1984) Nucl. Acids Res. 12:9323-9331, Taniguchi, et al. (1983) nature 302:305-310, Meada, et al. (1983) Biochem. Biophys. Res. Comm. 115:1040-1047, Devos, et al. (1983) Nucl. Acids Res. 11:4307-4323, and accession code Swissprot PO1585, which are each incorporated herein by reference.

The nucleotide and amino acid sequences of human IL-4 are well know and set forth in Arai, et al. (1989) J. Immunol. 142:274-282 Otsuka, et al. (1987) Nucl. Acids Res. 15:333-344, Yokota, et al. (1986) Proc. Natl. Acad. Sci USA 83:5894-5898, Noma, et al. (1984) Nature 319:640-646, Lee, et al. (1986) Proc. Natl. Acad. Sci. USA 83:2061-2063, and accession code Swissprot 05112 (the accession code for murine IL-4 is Swissprot 07750), Which are each incorporated herein by reference.

The nucleotide and amino acid sequences of human IL-5 are well known and set forth in Campbell, et al. (1987) Proc. Natl. Acad. Sci. USA 84:6629-6633, Tanabe, et al. (1987) J. Biol. Chem. 262:16580-16584, Campbell, et al. (1988) Eur. J. Biochem. 174:345-352, Azuma, et al. (1986) Nucl. Acids Res. 14:9149-9158, Yokota, et al. (1986) Proc. Natl. Acad. Sci. USA 84:7388-7392, and accession code Swissprot PO5113, which are each incorporated herein by reference.

The nucleotide and amino acid sequences of human IL-10 are well know and set forth in Viera, et al. (1991) Proc. Natl. Acad. Sci. USA 88:1172-1176, and accession code Swissprot P22301.

The nucleotide and amino acid sequences of human IL-15 are well known and set forth in Grabstein, et. al. (1994) Science 264:965-968, and accession code Swissprot UO3099, which are each incorporated herein by reference.

The nucleotide and amino acid sequences of human IL-18 are well known and set forth in Ushio, et al. (1996) J. Immunol. 156:4274-4279, and accession code D49950, which are each incorporated herein by reference.

The nucleotide and amino acid sequences of human TNF-α are well known and set forth in Pennica, (1984) Nature 312: 724-729, and accession code Swissprot PO1375, which are each incorporated herein by reference.

The nucleotide and amino acid sequences of human TNF-β are well known and set forth in Gray, (1984) Nature 312:721-724, and accession code Swessprot P01374, which are each incorporated herein by reference. ino acid sequences of human IL-10 are well know and set forth in Viera, et al. (1991) Proc. Natl. Acad. Sci. USA 88:1172-1176, and accession code Swissprot P22301, which are each incorporated herein by reference.

The complete coding sequence for human interleukin 12 mRNA, is set forth in Genbank Accession Number AF180563 (P40 mRNA) and AF180562 (P35 mRNA) and U.S. Pat. No. 5,840,530, which are each incorporated herein by reference.

Sequence information for MadCAM-1 is found at Genbank Accession Number U80016 (Leung, E., et al, Immunogenetics 46 (2), 111-119 (1997)), which are each incorporated herein by reference.

Sequence information for MadCAM-1 is found at Genbank Accession Number U43628 (Shyjan, A. M., et al, J. Immunol. 156 (8), 2851-2857 (1996)), which are each incorporated herein by reference.

Sequence information for NGF is found at Genbank Accession Number M57399 (Kretschmer, P. J., et al., Growth Factors 5, 99-114 (1991)), which are each incorporated herein by reference.

Sequence information for IL-7 is found at Genbank Accession Number J04156 (Goodwin, R. G., et al., Proc. Natl. Acad. Sci. U.S.A. 86 (1), 302-306 (1989)), which are each incorporated herein by reference.

Sequence information for VEGF is found at Genbank Accession Number M32977 (Leung, D. W., et al., Science 246, 1306-1309 (1989)), which are each incorporated herein by reference.

Sequence information for TNF-R is found at Genbank Accession Number M60275 (Gray, P. W., et al. Proc. Natl. Acad. Sci. U.S.A. 87, 7380-7384 (1990)), which are each incorporated herein by reference.

Sequence information for TNF-R is found at Genbank Accession Number M63121 (Himmler, A., et al. DNA Cell Biol. 9, 705-715 (1990)), which are each incorporated herein by reference.

Sequence information for Fas is found at Genbank Accession Number M67454 (Itoh, N., et al., Cell 66 (2), 233-243 (1991)), which are each incorporated herein by reference.

Sequence information for CD40L is found at Genbank Accession Number L07414 (Gauchat, J. F. M., et al. FEBS Lett, 315, 259-266 (1992), which are each incorporated herein by reference.

Sequence information for IL-4 is found at Genbank Accession Number M23442 (Arai, N., et al., J. Immunol. 142 (1), 274-282 (1989)), which are each incorporated herein by reference.

Sequence information for IL-4 is found at Genbank Accession Number M13982 (Yokota, T., et al. Proc. Natl. Acad. Sci. U.S.A. 83 (16), 5894-5898 (1986)), which are each incorporated herein by reference.

Sequence information for CSF is found at Genbank Accession Number M37435 (Wong, G. G., et al. Science 235 (4795), 1504-1508 (1987)), which are each incorporated herein by reference.

Sequence information for G-CSF is found at Genbank Accession Number X03656 (Nagata, S., et al, EMBO J. 5 (3), 575-581 (1986)), which are each incorporated herein by reference.

Sequence information for G-CSF is found at Genbank Accession Number X03655 (Nagata, S., et al., EMBO J. 5 (3), 575-581 (1986)), which are incorporated herein by reference.

Sequence information for GM-CSF is found at Genbank Accession Number M11220 (Lee, F., et al., Proc. Ntl. Acad. Sci. U.S.A. (13), 43604364 (1985)) which are incorporated herein by reference.

Sequence information for GM-CSF is found at Genbank Accession Number M10663 (Wong, G. G., et al., Science 228 (4701), 810-815 (1985)) which are incorporated herein by reference.

Sequence information for M-CSF is found at Genbank Accession Number M27087 (Takahashi, M., et al., Biochem. Biophys. Res. Commun. 161 (2), 892-901 (1989)) which are incorporated herein by reference.

Sequence information for M-CSF is found at Genbank Accession Number M37435 (Wong G. G., et al., Science 235 (4795), 1504-1508 (1987)) which are incorporated herein by reference.

Sequence information for LFA-3 is found at Genbank Accession Number Y00636 (Wallner, B. P., et al., J. Exp. Med. 166 (4), 923-932 (1987)) which are incorporated herein by reference.

Sequence information for ICAM-3 is found at Genbank Accession Number X69819 which are incorporated herein by reference.

Sequence information for ICAM-2 is found at Genbank Accession Number X15606 (Staunton, D. E., et al., Nature 339 (6219), 61-64 (1989)) which are incorporated herein by reference.

Sequence information for ICAM-1 is found at Genbank Accession Number J03132 (Staunton, D. E., et al., Cell 52 (6), 925-933 (1988)) which are incorporated herein by reference.

Sequence information for PECAM is found at Genbank Accession Number M28526 (Newman, P. J., et al., Science 247, 1219-1222 (1990) which are incorporated herein by reference.

Sequence information for P150.95 is found at Genbank Accession Number Y00093 (Corbi, A. L., et al., EMBO J. 6 (13), 4023-4028 (1987)) which are incorporated herein by reference.

Sequence information for Mac-1 is found at Genbank Accession Number J03925 (Corbi, A. L., et al., J. Biol. Chem. 263 (25), 12403-12411 (1988)) which are incorporated herein by reference.

Sequence information for LFA-1 is found at Genbank Accession Number Y00796 (Larson. R., et al., J. Cell Biol. 108 (2), 703-712 (1989)) which are incorporated herein by reference.

Sequence information for CD34 is found at Genbank Accession Number M81104 (Simmons, D. L. et al., J. Immunol. 148, 267-271 (1992)) which are incorporated herein by reference.

Sequence information for RANTES is found at Genbank Accession Number M21121 (Schall, T. J., et al., J. Immunol. 141, 1018-1025 (1988)) which are incorporated herein by reference.

Sequence information for IL-8 is found at Genbank Accession Number M28130 (Mukaida, N., et al., J. Immunol. 143 (4), 1366-1371 (1989)) which are incorporated herein by reference.

Sequence information for MIP-1α is found at Genbank Accession Number U72395 (Fridell, R. A., et al., J. Cell. Sci 110 (pt 11), 1325-1331 (1997)) which are incorporated herein by reference.

Sequence information for E-selecton is found at Genbank Accession Number M24736 (Bevilacqua, M. P., et al., Science 243 (4895), 1160-1165 (1989)) which are incorporated herein by reference.

Sequence information for CD2 is found at Genbank Accession Number M14362 (Sewell, W. A., et al. Proc. Natl. Acad. Sci. U.S.A. 83, 8718-8722 (1986); Proc. Natl. Acad. Sci. U.S.A. 84, 7256-7256 (1987)) which are incorporated herein by reference.

Sequence information for MCP-1 is found at Genbank Accession Number S69738 (Li, Y. S., et al., Mol. Cell. Biochem. 126 (1), 61-68 (1993)) which are incorporated herein by reference.

Sequence information for L-selection is found at Genbank Accession Number X16150 (Tedder, T. F., et al., J. Exp. Med. 170 (1), 123-133 (1989)) which are incorporated herein by reference.

Sequence information for P-selection is found at Genbank Accession Number M25322 (Johnston, G. I., et al., Cell 56, 1033-1044 (1989) which are incorporated herein by reference.

Sequence information for FLT is found at Genbank Accession Number X94263 (Mandriota, S. J., et al., J. Biol. Chem. 271 (19), 11500-11505 (1996)) which are incorporated herein by reference.

Sequence information for FLT is found at Genbank Accession Number X51602 (Shibuya, M. et al. Oncogene 5 (4), 519-524 (1990) Han, H. J., et al. Hum. Mol. Genet. 2 (12), 2204 (1993)) which are incorporated herein by reference.

Sequence information for Apo-1 is found at Genbank Accession Number X63717 (Oehm, et al, J. Biol. Chem., (1992), 267 (15), 10709-15) which are incorporated herein by reference.

Sequence information for Fas is found at Genbank Accession Number M67454 (Itoh, et al., Cell, (1991), 66 (2), 233-43) which are incorporated herein by reference.

Sequence information for TNFR-1 is found at Genbank Accession Number M67454 (Nophar, et al., EMBO J., 1990, 9(10), 3269-78) which are incorporated herein by reference.

Sequence information for p55 is found at Genbank Accession Number M58286 (Loetscher, et al., Cell, 1990, 61, 351-359) which are incorporated herein by reference.

Sequence information for WSL-1 is found at Genbank Accession Number Y09392 (Kitson, et al., Nature, 1996, 384 (6607), 372-5) which are incorporated herein by reference.

Sequence information for DR3 is found at Genbank Accession Number U72763 (Chinnaiyan, et al., Science, 1996, 274 (5829), 990-2) which are incorporated herein by reference.

Sequence information for TRAMP is found at Genbank Accession Number U75381 (Bodmer, et al., Immunity, 1997, 6 (1), 79-88) which are incorporated herein by reference.

Sequence information for Apo-3 is found at Genbank Accession Number U74611 (Marsters, et al., Curr. Biol., 1996, 6 (12), 1669-76) which are incorporated herein by reference.

Sequence information for AIR is found at Genbank Accession Number U78029 which is incorporated herein by reference.

Sequence information for LARD is found at Genbank Accession Number U94512 (Screaton, et al., Proc. Natl. Acad. Sci. USA, 1997, 94(9), 4615-19) which are incorporated herein by reference.

Sequence information for NGRF is found at Genbank Accession Number M14764 (Johnson, et al., Cell, 1986, 47(4), 545-554) which are incorporated herein by reference.

Sequence information for DR4(TRAIL) is found at Genbank Accession Number U90875 (Pan, et al., Science, 1997, 276(5309), 111-113) which are incorporated herein by reference.

Sequence information for DR5 is found at Genbank Accession Number AF012535 (Sheridan, et al., Science, 1997, 1 227(5327), 818-821) which are incorporated herein by reference.

Sequence information for KILLER is found at Genbank Accession Number AF022386 (Wu, et al., Nat. Genet. 17 (2), 141-143 (1997)) which are incorporated herein by reference.

Sequence information for TRAIL-R2 is found at Genbank Accession Number AF020501 which is incorporated herein by reference.

Sequence information for TRICK2 is found at Genbank Accession Number AF018657.

Sequence information for DR6 is found at Genbank Accession Number AF068868 which is incorporated herein by reference.

Sequence information for ICE is found at Genbank Accession Numbers U13697, U13698 and U13699 (Alnemri, E. S., et al., J. Biol. Chem. 270 (9), 4312-4317 (1995)) which are incorporated herein by reference.

Sequence information for VLA-1 is found at Genbank Accession Number X17033 (Takada., et al., J. Biol. Chem. 109 (1), 397-407 (1989)) which are incorporated herein by reference.

Sequence information for CD86 (B7.2) is found at Genbank Accession Number U04343 (Azuma, et al., Nature. 366 (6450), 76 (1993)) which are incorporated herein by reference.

TABLE 1

| | Picornavirus Family |
|---|---|
| Genera: | Rhinoviruses: (Medical) responsible for - 50% cases of the common cold. |
| | Etheroviruses: (Medical) includes polioviruses, coxsackieviruses, echoviruses, and human enteroviruses such as hepatitis A virus. |
| | Apthoviruses: (Veterinary) these are the foot and mouth disease viruses. |
| Target antigens: | VP1, VP2, VP3, VP4, VPG |
| | Calcivirus Family |
| Genera: | Norwalk Group of Viruses: (Medical) these viruses are an important causative agent of epidemic gastroenteritis. |
| | Togavirus Family |
| Genera: | Alphaviruses: (Medical and Veterinary) examples include Senilis viruses, RossRiver virus and Eastern & Western |

TABLE 1-continued

| | |
|---|---|
| | Equine encephalitis. |
| | Reovirug: (Medical) Rubella virus. |
| | Flariviridue Family |
| Examples include: | (Medical) dengue, yellow fever, Japanese encephalitis, St. Louis encephalitis and tick borne encephalitis viruses. West Nile virus (Genbank NC001563, AF533540, AF404757, AF404756, AF404755, AF404754, AF404753, AF481864, M12294, AF317203, AF196835, AF260969, AF260968, AF260967, AF206518 and AF202541) |
| Representative Target antigens: | E<br>NS5<br>C |
| Hepatitis C Virus: | (Medical) these viruses are not placed in a family yet but are believed to be either a togavirus or a flavivirus. Most similarity is with togavirus family. |
| | Coronavirus Family: |
| | (Medical and Veterinary)<br>Infectious bronchitis virus (poultry)<br>Porcine transmissible gastroenteric virus (pig)<br>Porcine hemaglutinating encephalomyelitis virus (pig)<br>Feline infectious peritonitis virus (cats)<br>Feline enteric coronavirus (cat)<br>Canine coronavirus (dog)<br>SARS associated coronavirus<br>The human respiratory coronaviruses cause ~40 cases of common cold.<br>EX. 224E, OC43<br>Note - coronaviruses may cause non-A, B or C hepatitis |
| Target antigens: | E1 - also called M or matrix protein<br>E2 - also called S or Spike protein<br>E3 - also called BE or hemagglutin-elterose glycoprotein (not present in all coronaviruses)<br>N - nucleocapsid |
| | Rhabdovirus Family |
| Genera: | Vesiliovirus<br>Lyssavirus: (medical and veterinary)<br>rabies |
| Target antigen: | G protein<br>N protein |
| | Filoviridue Family: |
| | (Medical)<br>Hemorrhagic fever viruses such as Marburg and Ebola virus |
| | Paramyxovirus Family: |
| Genera: | Paramyxovirus: (Medical and Veterinary)<br>Mumps virus, New Castle disease virus (important pathogen in chickens)<br>Morbillivirus: (Medical and Veterinary)<br>Measles, canine distemper<br>Pneuminvirus: (Medical and Veterinary)<br>Respiratory syncytial virus |
| | Orthomyxovirus Family |
| | (Medical)<br>The Influenza virus |
| | Bungavirus Family |
| Genera: | Bungavirus: (Medical) California encephalitis, LA Crosse<br>Phlebovirus: (Medical) Rift Valley Fever<br>Hantavirus: Puremala is a hemahagin fever virus<br>Nairvirus (Veterinary) Nairobi sheep disease<br>Also many unassigned bungaviruses |
| | Arenavirus Family |
| | (Medical)<br>LCM, Lassi fever virus |
| | Reovirus Family |
| Genera: | Reovirus: a possible human pathogen<br>Rotavirus: acute gastroenteritis in children<br>Orbiviruses: (Medical and Veterinary)<br>Colorado Tick fever, Lebombo (humans) equine encephalosis, blue tongue |

TABLE 1-continued

Retroyirus Family

| | |
|---|---|
| Sub-Family: | Oncorivirinal: (Veterinary) (Medical) feline leukemia virus, HTLVI and HTLVII |
| | Lentivirinal: (Medical and Veterinary) HIV, feline immunodeficiency virus, equine infections, anemia virus |
| | Spumavirinal |

Papovavirus Family

| | |
|---|---|
| Sub-Family: | Polyomaviruses: (Medical) BKU and JCU viruses |
| Sub-Family: | Papillomavirus: (Medical) many viral types associated with cancers or malignant progression of papilloma. |

Adenovirus (Medical)
EX AD7, ARD., O.B. - cause respiratory disease - some adenoviruses such as 275 cause enteritis

Parvovirus Family (Veterinary)
Feline parvovirus: causes feline enteritis
Feline panleucopeniavirus
Canine parvovirus
Porcine parvovirus

Herpesvirus Family

| | |
|---|---|
| Sub-Family: | alphaherpesviridue |
| Genera: | Simplexvirus (Medical) |
| | HSVI (Genbank X14112, NC001806), HSVII (NC001798) |
| | Varicellovinis: (Medical Veterinary) pseudorabies - varicella zoster |
| Sub-Family - | betaherpesviridue |
| Genera: | Cytomegalovirus (Medical) |
| | HCMV |
| | Muromegalovirus |
| Sub-Family. | Gammaherpesviridue |
| Genera: | Lymphocryptovirus (Medical) |
| | EBV - (Burkitts lympho) |
| | Rhadinovirus |

Poxvirus Family

| | |
|---|---|
| Sub-Family: | Chordopoxviridue (Medical - Veterinary) |
| Genera: | Variola. (Smallpox) |
| | Vaccinia (Cowpox) |
| | Parapoxivirus - Veterinary |
| | Auipoxvirus - Veterinary |
| | Capripoxvirus |
| | Leporipoxvirus |
| | Suipoxviru's |
| Sub-Family: | Entemopoxviridue |

Hepadnavirus Family

| | |
|---|---|
| Unclassified | Hepatitis B virus |
| | Hepatitis delta virus |

TABLE 2

| | |
|---|---|
| Bacterial pathogens | Pathogenic gram-positive cocci include: pneurnococcal; staphylococcal; and streptococcal. Pathogenic gram-negative cocci include: meningococcal; and gonococcal. |
| | Pathogenic enteric gram-negative bacilli include: enterobacteriaceae; *pseudomonas*, acinetobacteria and eikenella, melioidosis;, sahnonella; shigellosis; hemophilus; chancroid; brucellosis; tularemia; yersinia (pasteurella); streptobacillus mortiliformis and spirillum; listeria monocytogenes; erysipelothrix rhusiopathiae; diphtheria, cholera, anthrax; donovanosis (granuloma inguinale); and bartonellosis. Pathogenic anaerobic bacteria include: tetanus; botulism; other clostridia; tuberculosis; leprosy; and other mycobacteria. Pathogenic spirochetal diseases include: syphilis; - treponematoses: yaws, pinta and endemic syphilis; and leptospirosis. |
| | Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma, and |

TABLE 2-continued

| | |
|---|---|
| | chromomycosis; and dermatophytosis.<br>Rickettsial infections include rickettsial and rickettsioses.<br>Examples of mycoplasma and chlarnydial infections include:<br>mycoplasma pneurnoniae; lymphogranuloma venereum;<br>psittacosis; and perinatal chlamydial infections. |
| Pathogenic eukaryotes | Pathogenic protozoans and helminths and infections thereby include:<br>amebiasis; malaria; leishmaniasis; trypanosomiasis; toxoplasmosis;<br>pneurnocystis carinii; babesiosis; giardiasis; trichinosis; filariasis;<br>schistosomiasis; nematodes; trematodes or flukes; and cestode<br>(tapeworm) infections. |

The invention claimed is:

1. An isolated nucleic acid molecule comprising a nucleic acid sequence selected from the group consisting of:
   a nucleic acid sequence that encodes a fusion protein that consists of a non-IgE protein sequences linked to an IgE signal peptide that is from the same species as the non-IgE protein; and
   a nucleic acid sequence that encodes a fusion protein that consists of a non-IgE protein sequences linked to an IgE signal peptide, wherein the non-IgE protein is an immunomodulating protein selected from the group consisting of cytokines, chemokines, cellular death receptors, cellular adhesion molecules, cellular growth factors, cellular growth factor receptors, protein kinases and enzymes or functional fragment thereof.

2. The isolated nucleic acid molecule of claim 1 wherein said isolated nucleic acid molecule is a plasmid.

3. The nucleic acid molecule of claim 1 incorporated into a viral vector.

4. A composition comprising a nucleic acid molecule of claim 1 and a nucleic acid molecule that comprises a nucleic acid sequence that encodes an immunogen.

5. The composition of claim 4 wherein said composition comprises a nucleic acid molecule that encodes an immunogen, wherein said immunogen is a pathogen antigen, a cancer-associated antigen or an antigen linked to cells associated with autoimmune diseases.

6. The composition of claim 5 wherein said immunogen is a pathogen antigen is from a pathogen selected from the group consisting of HIV, HSV, HCV, and WNV.

7. The isolated nucleic acid molecule of claim 1 comprising a nucleic acid sequence that encodes a fusion protein that consists of a non-IgE protein sequences linked to an IgE signal peptide that is from the same species as the non-IgE protein.

8. The isolated nucleic acid molecule of claim 7 wherein said isolated nucleic acid molecule is a plasmid.

9. The nucleic acid molecule of claim 7 incorporated into a viral vector.

10. A composition comprising a nucleic acid molecule of claim 7 and a nucleic acid molecule that comprises a nucleic acid sequence that encodes an immunogen.

11. The composition of claim 10 wherein said composition comprises a nucleic acid molecule that encodes an immunogen, wherein said immunogen is a pathogen antigen, a cancer-associated antigen or an antigen linked to cells associated with autoimmune diseases.

12. The composition of claim 11 wherein said immunogen is a pathogen antigen is from a pathogen selected from the group consisting of HIV, HSV, HCV, and WNV.

13. The isolated nucleic acid molecule of claim 1 comprising a nucleic acid sequence that encodes a fusion protein that consists of a non-IgE protein sequences linked to a IgE signal peptide wherein the non-IgE protein is an immunomodulating protein.

14. The isolated nucleic acid molecule of claim 13 wherein said isolated nucleic acid molecule is a plasmid.

15. The nucleic acid molecule of claim 13 incorporated into a viral vector.

16. A composition comprising a nucleic acid molecule of claim 13 and a nucleic acid molecule that comprises a nucleic acid sequence that encodes an immunogen.

17. The composition of claim 16 wherein said composition comprises a nucleic acid molecule that encodes an immunogen, wherein said immunogen is a pathogen antigen, a cancer-associated antigen or an antigen linked to cells associated with autoimmune diseases.

18. The composition of claim 17 wherein said immunogen is a pathogen antigen is from a pathogen selected from the group consisting of HIV, HSV, HCV, and WNV.

19. The isolated nucleic acid molecule of claim 1 wherein the non-IgE protein is an immunomodulating protein selected from the group consisting of an enzyme, functional fragment thereof, IL-15, CD40L, TRAIL; TRAILrecDRC5, TRAIL-R2, TRAIL-R3, TRAIL-R4, RANK, RANK LIGAND, Ox40, Ox40 LIGAND, NKG2D, F461811 or MICA, MICB, NKG2A, NKG2B, NKG2C, NKG2E, NKG2F, CD30, CD153 (CD30L), Fos, cjun, Sp-1, Ap1, Ap-2, p38, p65Rel, MyD88, IRAK, TRAF6, IkB, NIK, SAP K, SAP1, JNK2, JNK1B2, JNK1B1, JNK2B2, JNK2B1, JNK1A2, JNK2A1, JNK3A1, JNK3A2, NF-kappa-B2, p49 splice form, NF-kappa-B2, p100 splice form, NF-kappa-B2, p105 splice form, NF-kappa-B 50K chain precursor, NFkB p50, human IL-1a, human IL-2, human IL-4, murine IL-4, human IL-5, human IL-10, human IL-15, human IL-18, human TNF-a, human TNF-P, human interleukin 12, MadCAM-1, NGF IL-7, VEGF, TNF-R, Fas, CD40L, IL-4, CSF, G-CSF, GM-CSF, M-CSF, LFA-3, ICAM-3, ICAM-2, ICAM-1, PECAM, P150.95, Mac-1, LFA-1, CD34, RANTES, IL-8, MIP-1a, E-selecton, CD2, MCP-1, L-selecton, P-selecton, FLT, Apo-1, Fas, TNFR-1, p55, WSL-1, DR3, TRAMP, Apo-3, AIR, LARD, NGRF, DR4 (TRAIL), DR5, KILLER, TRAIL-R2, TRICK2, DR6, ICE, VLA-1, and CD86 (B7. 2).

\* \* \* \* \*